(12) United States Patent
Single et al.

(10) Patent No.: US 10,206,596 B2
(45) Date of Patent: Feb. 19, 2019

(54) METHOD AND SYSTEM FOR CONTROLLING ELECTRICAL CONDITIONS OF TISSUE

(71) Applicant: Saluda Medical Pty Ltd, Artarmon (AU)

(72) Inventors: Peter Scott Vallack Single, Artarmon (AU); James Hamilton Laird-Wah, Artarmon (AU)

(73) Assignee: Saluda Medical Pty Ltd, Artarmon (AU)

( * ) Notice: Subject to any disclaimer, the term of this patent is extended or adjusted under 35 U.S.C. 154(b) by 269 days.

(21) Appl. No.: 14/440,873

(22) PCT Filed: Nov. 6, 2013

(86) PCT No.: PCT/AU2013/001279
§ 371 (c)(1),
(2) Date: May 5, 2015

(87) PCT Pub. No.: WO2014/071445
PCT Pub. Date: May 15, 2014

(65) Prior Publication Data
US 2015/0313487 A1    Nov. 5, 2015

(30) Foreign Application Priority Data
Nov. 6, 2012 (AU) ................. 2012904836
Nov. 6, 2012 (AU) ................. 2012904838

(51) Int. Cl.
*A61B 5/04* (2006.01)
*A61N 1/36* (2006.01)
(Continued)

(52) U.S. Cl.
CPC ........ *A61B 5/04001* (2013.01); *A61B 5/4848* (2013.01); *A61B 5/686* (2013.01);
(Continued)

(58) Field of Classification Search
CPC ............ A61B 5/04001; A61B 5/04004; A61B 5/4041; A61B 5/7203; A61B 5/7217;
(Continued)

(56) References Cited

U.S. PATENT DOCUMENTS 3,736,434 A    5/1973    Darrow
3,817,254 A    6/1974    Maurer
(Continued)

FOREIGN PATENT DOCUMENTS

EP    0219084    4/1987
EP    0998958 B1    8/2005
(Continued)

OTHER PUBLICATIONS

Extended European Search Report for European Application No. 13852669.4, Search completed Jun. 8, 2016, dated Jun. 22, 2016, 09 Pgs.
(Continued)

*Primary Examiner* — Devin Henson
(74) *Attorney, Agent, or Firm* — KPPB LLP

(57) ABSTRACT

An implantable device for controlling electrical conditions of body tissue. A feedback sense electrode and a compensation electrode are positioned proximal to the tissue to make electrical contact with the tissue. A feedback amplifier is referenced to ground, and takes as an input a feedback signal from the feedback sense electrode. The output of the feedback amplifier is connected to the compensation electrode. The feedback amplifier thus drives the neural tissue via the compensation electrode in a feedback arrangement which seeks to drive the feedback signal to ground, or other desired electrical value.

8 Claims, 9 Drawing Sheets

(51) Int. Cl.
   *A61B 5/00* (2006.01)
   *A61B 5/0428* (2006.01)

(52) U.S. Cl.
   CPC ........ *A61B 5/7217* (2013.01); *A61N 1/36125* (2013.01); *A61N 1/36132* (2013.01); *A61B 5/04004* (2013.01); *A61B 5/0428* (2013.01); *A61B 5/4041* (2013.01); *A61B 5/7203* (2013.01); *A61B 5/7225* (2013.01); *A61B 5/7228* (2013.01); *A61B 5/7296* (2013.01); *A61N 1/36139* (2013.01); *A61N 1/36146* (2013.01)

(58) Field of Classification Search
   CPC ... A61B 5/7225; A61B 5/7228; A61B 5/7296; A61N 1/36125; A61N 1/36139; A61N 1/36146
   See application file for complete search history.

(56) References Cited

U.S. PATENT DOCUMENTS

| | | |
|---|---|---|
| 3,898,472 A | 8/1975 | Long |
| 4,158,196 A | 6/1979 | Crawford, Jr. |
| 4,418,695 A | 12/1983 | Buffet |
| 4,474,186 A | 10/1984 | Ledley et al. |
| 4,628,934 A | 12/1986 | Pohndorf et al. |
| 4,807,643 A | 2/1989 | Rosier |
| 4,856,525 A | 8/1989 | Van et al. |
| 5,113,859 A | 5/1992 | Funke |
| 5,139,020 A | 8/1992 | Koestner et al. |
| 5,143,081 A | 9/1992 | Young et al. |
| 5,156,154 A | 10/1992 | Valenta, Jr. et al. |
| 5,172,690 A | 12/1992 | Nappholz et al. |
| 5,184,615 A | 2/1993 | Nappholz et al. |
| 5,188,106 A | 2/1993 | Nappholz et al. |
| 5,215,100 A | 6/1993 | Spitz |
| 5,324,311 A | 6/1994 | Acken |
| 5,417,719 A | 5/1995 | Hull et al. |
| 5,431,693 A | 7/1995 | Schroeppel |
| 5,458,623 A | 10/1995 | Lu et al. |
| 5,476,486 A | 12/1995 | Lu et al. |
| 5,497,781 A | 3/1996 | Chen et al. |
| 5,638,825 A | 6/1997 | Yamazaki et al. |
| 5,702,429 A | 12/1997 | King et al. |
| 5,758,651 A | 6/1998 | Nygard et al. |
| 5,776,170 A | 7/1998 | Macdonald et al. |
| 5,785,651 A | 7/1998 | Kuhn et al. |
| 5,792,212 A | 8/1998 | Weijand et al. |
| 5,814,092 A | 9/1998 | King |
| 5,913,882 A | 6/1999 | King |
| 5,999,848 A | 12/1999 | Gord et al. |
| 6,020,857 A | 2/2000 | Podger |
| 6,027,456 A | 2/2000 | Feler et al. |
| 6,038,480 A | 3/2000 | Hrdlicka et al. |
| 6,066,163 A | 5/2000 | John |
| 6,114,164 A | 9/2000 | Dennis et al. |
| 6,144,881 A | 11/2000 | Hemming et al. |
| 6,157,861 A | 12/2000 | Faltys et al. |
| 6,212,431 B1 | 4/2001 | Hahn et al. |
| 6,246,912 B1 | 6/2001 | Sluijter et al. |
| 6,381,496 B1 | 4/2002 | Meadows et al. |
| 6,463,328 B1 | 10/2002 | John |
| 6,473,649 B1 | 10/2002 | Gryzwa et al. |
| 6,473,653 B1 | 10/2002 | Schallhorn et al. |
| 6,493,576 B1 | 12/2002 | Dankwart-Eder |
| 6,522,932 B1 | 2/2003 | Kuzma |
| 6,600,955 B1 | 7/2003 | Zierhofer et al. |
| 6,658,293 B2 | 12/2003 | Vonk et al. |
| 6,675,046 B2 | 1/2004 | Holsheimer |
| 6,782,292 B2 | 8/2004 | Whitehurst |
| 6,898,582 B2 | 5/2005 | Lange et al. |
| 7,089,059 B1 | 8/2006 | Pless |
| 7,171,261 B1 | 1/2007 | Litvak et al. |
| 7,231,254 B2 | 6/2007 | DiLorenzo et al. |
| 7,286,876 B2 | 10/2007 | Yonce et al. |
| 7,412,287 B2 | 8/2008 | Yonce et al. |
| 7,450,992 B1 | 11/2008 | Cameron |
| 7,734,340 B2 | 6/2010 | De Ridder |
| 7,742,810 B2 | 6/2010 | Moffitt |
| 7,792,584 B2 | 9/2010 | Van Oort et al. |
| 7,818,052 B2 | 10/2010 | Litvak et al. |
| 7,831,305 B2 | 11/2010 | Gliner |
| 7,835,804 B2 | 11/2010 | Fridman et al. |
| 8,190,251 B2 | 5/2012 | Molnar et al. |
| 8,224,459 B1 | 7/2012 | Pianca et al. |
| 8,239,031 B2 | 8/2012 | Fried et al. |
| 8,359,102 B2 | 1/2013 | Thacker et al. |
| 8,494,645 B2 | 7/2013 | Spitzer et al. |
| 8,588,929 B2 | 11/2013 | Davis et al. |
| 8,670,830 B2 | 3/2014 | Carlson et al. |
| 8,886,323 B2 | 11/2014 | Wu et al. |
| 9,155,892 B2 | 10/2015 | Parker et al. |
| 9,381,356 B2 | 7/2016 | Parker et al. |
| 9,386,934 B2 | 7/2016 | Parker et al. |
| 9,974,455 B2 | 5/2018 | Parker et al. |
| 2002/0055688 A1 | 5/2002 | Katims |
| 2002/0099419 A1 | 7/2002 | Ayal et al. |
| 2002/0193670 A1 | 12/2002 | Garfield et al. |
| 2003/0032889 A1 | 2/2003 | Wells |
| 2003/0045909 A1 | 3/2003 | Gross et al. |
| 2003/0139781 A1 | 7/2003 | Bradley et al. |
| 2003/0195580 A1 | 10/2003 | Bradley et al. |
| 2004/0088017 A1 | 5/2004 | Sharma et al. |
| 2004/0122482 A1 | 6/2004 | Tung et al. |
| 2004/0158298 A1 | 8/2004 | Gliner |
| 2004/0225211 A1 | 11/2004 | Gozani et al. |
| 2004/0254494 A1 | 12/2004 | Spokoyny et al. |
| 2005/0010265 A1 | 1/2005 | Baru Fassio |
| 2005/0021104 A1 | 1/2005 | DiLorenzo |
| 2005/0065427 A1 | 3/2005 | Magill |
| 2005/0070982 A1 | 3/2005 | Heruth et al. |
| 2005/0075683 A1 | 4/2005 | Miesel et al. |
| 2005/0101878 A1 | 5/2005 | Daly et al. |
| 2005/0113877 A1 | 5/2005 | Giardiello et al. |
| 2005/0137670 A1 | 6/2005 | Christopherson et al. |
| 2005/0149154 A1 | 7/2005 | Cohen |
| 2005/0192567 A1 | 9/2005 | Katims |
| 2005/0203600 A1 | 9/2005 | Wallace |
| 2005/0209655 A1 | 9/2005 | Bradley et al. |
| 2005/0282149 A1 | 12/2005 | Kovacs et al. |
| 2006/0009820 A1 | 1/2006 | Royle et al. |
| 2006/0020291 A1 | 1/2006 | Gozani |
| 2006/0135998 A1 | 6/2006 | Libbus et al. |
| 2006/0195159 A1 | 8/2006 | Bradley et al. |
| 2006/0212089 A1 | 9/2006 | Tass |
| 2006/0217782 A1 | 9/2006 | Boveja et al. |
| 2006/0264752 A1 | 11/2006 | Rubinsky et al. |
| 2006/0287609 A1 | 12/2006 | Litvak et al. |
| 2007/0021800 A1 | 1/2007 | Bradley et al. |
| 2007/0073354 A1 | 3/2007 | Knudson et al. |
| 2007/0100378 A1 | 5/2007 | Maschino |
| 2007/0178579 A1 | 8/2007 | Ross et al. |
| 2007/0208394 A1 | 9/2007 | King et al. |
| 2007/0225767 A1 | 9/2007 | Daly |
| 2007/0244410 A1 | 10/2007 | Fridman |
| 2007/0250120 A1 | 10/2007 | Flach et al. |
| 2007/0255372 A1 | 11/2007 | Metzler et al. |
| 2007/0282217 A1 | 12/2007 | McGinnis et al. |
| 2007/0287931 A1 | 12/2007 | Dilorenzo |
| 2008/0021292 A1 | 1/2008 | Stypulkowski |
| 2008/0051647 A1 | 2/2008 | Wu et al. |
| 2008/0064947 A1 | 3/2008 | Heruth et al. |
| 2008/0097529 A1 | 4/2008 | Parramon et al. |
| 2008/0147155 A1 | 6/2008 | Swoyer |
| 2008/0183076 A1 | 7/2008 | Witte |
| 2008/0208304 A1 | 8/2008 | Zdravkovic et al. |
| 2008/0234780 A1 | 9/2008 | Smith et al. |
| 2008/0275527 A1 | 11/2008 | Greenberg et al. |
| 2008/0294221 A1 | 11/2008 | Kilgore |
| 2008/0300655 A1 | 12/2008 | Cholette |
| 2009/0033486 A1 | 2/2009 | Costantino et al. |
| 2009/0082691 A1 | 3/2009 | Denison et al. |
| 2009/0157155 A1 | 6/2009 | Bradley |

(56) References Cited

U.S. PATENT DOCUMENTS

| | | |
|---|---|---|
| 2009/0270957 A1 | 10/2009 | Pianca |
| 2009/0287277 A1 | 11/2009 | Conn et al. |
| 2009/0299214 A1 | 12/2009 | Wu et al. |
| 2009/0306491 A1 | 12/2009 | Haggers |
| 2010/0010388 A1 | 1/2010 | Panken et al. |
| 2010/0058126 A1 | 3/2010 | Chang et al. |
| 2010/0069835 A1 | 3/2010 | Parker |
| 2010/0069996 A1 | 3/2010 | Strahl |
| 2010/0070007 A1 | 3/2010 | Parker |
| 2010/0070008 A1 | 3/2010 | Parker |
| 2010/0106231 A1 | 4/2010 | Torgerson |
| 2010/0114258 A1 | 5/2010 | Donofrio et al. |
| 2010/0125313 A1 | 5/2010 | Lee et al. |
| 2010/0125314 A1 | 5/2010 | Bradley et al. |
| 2010/0145222 A1 | 6/2010 | Brunnett et al. |
| 2010/0152808 A1 | 6/2010 | Boggs |
| 2010/0179626 A1 | 7/2010 | Pilarski |
| 2010/0191307 A1 | 7/2010 | Fang et al. |
| 2010/0204748 A1 | 8/2010 | Lozano et al. |
| 2010/0222844 A1 | 9/2010 | Troosters et al. |
| 2010/0222858 A1 | 9/2010 | Meloy |
| 2010/0249643 A1 | 9/2010 | Gozani et al. |
| 2010/0249867 A1 | 9/2010 | Wanasek |
| 2010/0258342 A1 | 10/2010 | Parker |
| 2010/0262208 A1 | 10/2010 | Parker |
| 2010/0262214 A1 | 10/2010 | Robinson |
| 2010/0280570 A1 | 11/2010 | Sturm et al. |
| 2010/0286748 A1 | 11/2010 | Midani et al. |
| 2010/0331604 A1 | 12/2010 | Okamoto et al. |
| 2010/0331926 A1 | 12/2010 | Lee et al. |
| 2011/0004207 A1 | 1/2011 | Wallace et al. |
| 2011/0021943 A1 | 1/2011 | Lacour et al. |
| 2011/0028859 A1 | 2/2011 | Chian |
| 2011/0087085 A1 | 4/2011 | Tsampazis et al. |
| 2011/0093042 A1 | 4/2011 | Torgerson et al. |
| 2011/0106100 A1 | 5/2011 | Bischoff |
| 2011/0184488 A1 | 7/2011 | De Ridder et al. |
| 2011/0204811 A1 | 8/2011 | Pollmann-Retsch |
| 2011/0224749 A1 | 9/2011 | Ben-David et al. |
| 2011/0264165 A1 | 10/2011 | Molnar et al. |
| 2011/0313310 A1 | 12/2011 | Tomita |
| 2011/0313483 A1 | 12/2011 | Hincapie et al. |
| 2012/0029377 A1 | 2/2012 | Polak |
| 2012/0101552 A1 | 4/2012 | Lazarewicz et al. |
| 2012/0109236 A1 | 5/2012 | Jacobson et al. |
| 2012/0253423 A1 | 10/2012 | Youn et al. |
| 2012/0277621 A1 | 11/2012 | Gerber et al. |
| 2012/0277823 A1 | 11/2012 | Gerber et al. |
| 2013/0053722 A1 | 2/2013 | Carlson et al. |
| 2013/0060302 A1 | 3/2013 | Polefko et al. |
| 2013/0172774 A1 | 7/2013 | Crowder et al. |
| 2013/0289661 A1 | 10/2013 | Griffith et al. |
| 2013/0289683 A1 | 10/2013 | Parker et al. |
| 2014/0142447 A1 | 5/2014 | Takahashi et al. |
| 2014/0194771 A1 | 7/2014 | Parker et al. |
| 2014/0194772 A1 | 7/2014 | Single et al. |
| 2014/0236042 A1 | 8/2014 | Parker et al. |
| 2014/0236257 A1 | 8/2014 | Parker et al. |
| 2014/0243926 A1 | 8/2014 | Carcieri |
| 2014/0243931 A1 | 8/2014 | Parker et al. |
| 2014/0276195 A1 | 9/2014 | Papay et al. |
| 2014/0277250 A1 | 9/2014 | Su et al. |
| 2014/0288551 A1 | 9/2014 | Bharmi et al. |
| 2014/0288577 A1 | 9/2014 | Robinson et al. |
| 2014/0296737 A1 | 10/2014 | Parker et al. |
| 2014/0358024 A1 | 12/2014 | Nelson et al. |
| 2015/0018699 A1 | 1/2015 | Zeng et al. |
| 2015/0164354 A1 | 6/2015 | Parker et al. |
| 2015/0174396 A1 | 6/2015 | Fisher et al. |
| 2015/0238304 A1 | 8/2015 | Lamraoui |
| 2015/0282725 A1 | 10/2015 | Single |
| 2015/0374999 A1 | 12/2015 | Parker |
| 2016/0166164 A1 | 6/2016 | Obradovic et al. |
| 2016/0287126 A1 | 10/2016 | Parker et al. |
| 2016/0287182 A1 | 10/2016 | Single |
| 2017/0001017 A9 | 1/2017 | Parker et al. |
| 2017/0049345 A1 | 2/2017 | Single |
| 2017/0071490 A1 | 3/2017 | Parker et al. |
| 2017/0135624 A1 | 5/2017 | Parker |
| 2017/0216587 A1 | 8/2017 | Parker |
| 2018/0110987 A1 | 4/2018 | Parker |
| 2018/0117335 A1 | 5/2018 | Parker et al. |
| 2018/0132747 A1 | 5/2018 | Parker et al. |
| 2018/0132760 A1 | 5/2018 | Parker |
| 2018/0133459 A1 | 5/2018 | Parker et al. |

FOREIGN PATENT DOCUMENTS

| | | |
|---|---|---|
| EP | 2019716 A | 11/2007 |
| EP | 2243510 A2 | 10/2010 |
| EP | 2443995 A2 | 4/2012 |
| JP | 2013527784 A | 7/2013 |
| WO | 1983003191 A | 9/1983 |
| WO | 9612383 A1 | 4/1996 |
| WO | 2000002623 A1 | 1/2000 |
| WO | 2002036003 A1 | 11/2001 |
| WO | 2002038031 | 5/2002 |
| WO | 2002049500 A2 | 6/2002 |
| WO | 2003028521 A2 | 4/2003 |
| WO | 2003043690 | 5/2003 |
| WO | 2003103484 | 12/2003 |
| WO | 2004021885 A1 | 3/2004 |
| WO | 20040103455 | 12/2004 |
| WO | 2005032656 A1 | 4/2005 |
| WO | 2005105202 A1 | 11/2005 |
| WO | 2006091636 A2 | 8/2006 |
| WO | 2007064936 A1 | 6/2007 |
| WO | 2007127926 A2 | 11/2007 |
| WO | 2007130170 A1 | 11/2007 |
| WO | 2008004204 A1 | 1/2008 |
| WO | 2008049199 A1 | 5/2008 |
| WO | 2009002072 A2 | 12/2008 |
| WO | 2009002579 A1 | 12/2008 |
| WO | 2009010870 A2 | 1/2009 |
| WO | 2009130515 A2 | 10/2009 |
| WO | 2009146427 A1 | 12/2009 |
| WO | 2010013170 A1 | 2/2010 |
| WO | 2010044989 A2 | 4/2010 |
| WO | 2010051392 A1 | 5/2010 |
| WO | 2010057046 A2 | 5/2010 |
| WO | 2010124139 A1 | 10/2010 |
| WO | 2010138915 A1 | 12/2010 |
| WO | 2011011327 A1 | 1/2011 |
| WO | 2011066477 A1 | 6/2011 |
| WO | 2011066478 A1 | 6/2011 |
| WO | 2011112843 A1 | 9/2011 |
| WO | 2011119251 A2 | 9/2011 |
| WO | 2011159545 A2 | 12/2011 |
| WO | 2012027791 A1 | 3/2012 |
| WO | 2012155183 A1 | 11/2012 |
| WO | 2012155184 A1 | 11/2012 |
| WO | 2012155185 A1 | 11/2012 |
| WO | 2012155187 A1 | 11/2012 |
| WO | 2012155188 A1 | 11/2012 |
| WO | 2012155189 A1 | 11/2012 |
| WO | 2012155190 A1 | 11/2012 |
| WO | 2013063111 A1 | 5/2013 |
| WO | 2013075171 A1 | 5/2013 |
| WO | 2014071445 A1 | 5/2014 |
| WO | 2014071446 A1 | 5/2014 |
| WO | 2014143577 A1 | 9/2014 |
| WO | 1993001863 A1 | 2/2015 |
| WO | 2015070281 A1 | 5/2015 |
| WO | 2015074121 A1 | 5/2015 |
| WO | 2015109239 A1 | 7/2015 |
| WO | 2015143509 A1 | 10/2015 |
| WO | 2015168735 A1 | 11/2015 |
| WO | 2016011512 | 1/2016 |
| WO | 2016077882 A1 | 5/2016 |
| WO | 2016090420 A1 | 6/2016 |
| WO | 2016090436 A1 | 6/2016 |
| WO | 2016115596 A1 | 7/2016 |
| WO | 2016161484 A2 | 10/2016 |

(56) References Cited

FOREIGN PATENT DOCUMENTS

| WO | 2016191807 A1 | 12/2016 |
|---|---|---|
| WO | 2016191808 A1 | 12/2016 |
| WO | 2016191815 A1 | 12/2016 |

OTHER PUBLICATIONS

Extended European Search Report for European Application no. 13853514.1, Search completed Jun. 8, 2016, dated Jun. 15, 2016, 07 Pgs.
Van den Berg et al., "Nerve fiber size-related block of action currents by phenytoin in mammalian nerve", Nov. 1994 (Nov. 1994). Epilepsia Nov.-Dec. 1994. vol. 35. Nr. 6. pp. 1279-1288. XP002758489.I SSN: 0013-9580 figure 1.
Vleggeert, Lankamp et al., "Electrophysiology and morphometry of the Aalpha- and Abeta-fiber populations in the normal and regenerating rat sciatic nerve", Experimental Neurology. Academic Press, New York, NY, US. vol. 187. No. 2. Jun. 1, 2004 (Jun. 1, 2004). pp. 337-349. XP004620610. ISSN: 0014-4886 DOI: 10.1016/J.EXPNEUROL.2004.01.019 figure 1.
International Search Report, International Search Report & Written Opinion for International Application No. PCT/AU2013/001280, Search Completed Jan. 16, 2014, dated Jan. 16, 2014, 8 Pgs.
International Search Report, International Search Report & Written Opinion for International Application PCT/AU2013/001279, Search Completed Jan. 9, 2014, dated Jan. 9, 2014, 9 Pgs.
Markandey, Vishal, "ECG Implementation on the TMS320C5515 DSP Medical Development Kit (MDK)", Texas Instruments Application Report Jun. 2010, 35 pgs.
Texas Instruments, "Precision, Low Power Instrumentation Amplifiers", Texas Instruments SBOS051B Oct. 1995, Revised Feb. 2005, 20 pgs.
International Type Search Report for International Application No. AU 2015902393, Search completed May 16, 2016, dated May 16, 2016, 8 Pgs.
International Preliminary Report on Patentability for International Application No. PCT/AU2011/001127, dated Mar. 5, 2013, 9 pgs.
International Preliminary Report on Patentability for International Application No. PCT/AU2012/000511, dated Nov. 19, 2013, 6 pgs.
International Preliminary Report on Patentability for International Application No. PCT/AU2012/000512, dated Nov. 19, 2013, 8 pgs.
International Preliminary Report on Patentability for International Application No. PCT/AU2012/000513, dated Nov. 19, 2013, 11 pgs.
International Preliminary Report on Patentability for International Application No. PCT/AU2012/000515, dated Nov. 19, 2013, 5 pgs.
International Preliminary Report on Patentability for International Application No. PCT/AU2012/000516, dated Nov. 19, 2013, 9 pgs.
International Preliminary Report on Patentability for International Application No. PCT/AU2012/000517, dated Nov. 19, 2013, 6 pgs.
International Preliminary Report on Patentability for International Application No. PCT/AU2012/000518, dated Nov. 19, 2013, 11 pgs.
International Preliminary Report on Patentability for International Application No. PCT/AU2013/001279, dated May 12, 2015, 6 pgs.
International Preliminary Report on Patentability for International Application No. PCT/AU2013/001280, dated May 12, 2015, 6 pgs.
International Preliminary Report on Patentability for International Application No. PCT/AU2014/001049, dated May 17, 2016, 5 pgs.
International Preliminary Report on Patentability for International Application No. PCT/AU2014/050369, dated May 24, 2016, 8 pgs.
International Preliminary Report on Patentability for International Application No. PCT/AU2015/050135, dated Oct. 4, 2016, 13 pgs.
International Preliminary Report on Patentability for International Application No. PCT/AU2015/050215, dated Nov. 8, 2016, 4 pgs.
International Preliminary Report on Patentability for International Application No. PCT/AU2015/050422, dated Jan. 31, 2017, 8 pgs.
International Preliminary Report on Patentability for International Application No. PCT/AU2015/050724, dated May 23, 2017, 5 pgs.
International Preliminary Report on Patentability for International Application No. PCT/AU2015/050787, dated Jun. 13, 2017, 6 pgs.
International Preliminary Report on Patentability for International Application No. PCT/AU2016/050019, dated Jul. 25, 2017, 9 pgs.
International Preliminary Report on Patentability for International Application No. PCT/AU2016/050263, dated Oct. 10, 2017, 9 pgs.
International Search Report and Written Opinion for International Application No. PCT/AU2016/050263, Search completed Nov. 16, 2016, dated Nov. 16, 2016, 8 Pgs.
International Search Report and Written Opinion for International Application No. PCT/AU2016/050430, Search completed Aug. 16, 2016, dated Aug. 16, 2016, 10 Pgs.
International Search Report and Written Opinion for International Application No. PCT/AU2016/050431, Search completed Aug. 16, 2016, dated Aug. 16, 2016, 11 Pgs.
International Search Report and Written Opinion for International Application No. PCT/AU2016/050439, Search completed Jul. 15, 2016, dated Jul. 15, 2016, 8 Pgs.
Alam et al., "Evaluation of optimal electrode configurations for epidural spinal cord stimulation in cervical spinal cord injured rats", Journal of Neuroscience Methods, Mar. 2015, 28 pgs.
Fisher, "F-Waves—Physiology and Clinical Uses", TheScientificWorldJournal, (2007) 7, pp. 144-160.
Gad et al., "Development of a multi-electrode array for spinal cord epidural stimulation to facilitate stepping and standing after a complete spinal cord injury in adult rats", Journal of NeuroEngineering and Rehabilitation 2013, 10:2, 18 pgs.
Sayenko et al., "Neuromodulation of evoked muscle potentials induced by epidural spinal-cord stimulation in paralyzed individuals", Journal of Neurophysiology, vol. 111, No. 5, 2014, pp. 1088-1099, First published Dec. 11, 2013.
Struijk et al., "Excitation of Dorsal Root Fibers in Spinal Cord Stimulation: a Theoretical Study", IEEE Transactions on Biomedical Engineering, Jul. 1993, vol. 40, No. 7, pp. 632-639.
Yamada et al., "Extraction and Analysis of the Single Motor Unit F-Wave of the Median Nerve", EMG Methods for Evaluating Muscle and Nerve Function, InTech, 2012, 15 pgs.
International Preliminary Report on Patentability for International Application No. PCT/AU2015/050753, dated Jun. 13, 2017, 7 pgs.
European Search Report for European Application 12785619.3 Search Completed Oct. 13, 2014, dated Oct. 23, 2014, 7 pgs.
European Search Report for European Application 12785669.8 Search Completed Sep. 22, 2014, dated Sep. 29, 2014, 5 pgs.
Extended European Search Report for EP Application 12785483.4 completed Sep 16, 2014, 7 pgs.
Extended European Search Report for European Application No. 11820923.8, report completed Dec. 9, 2013, dated Dec. 17, 2013, 6 pgs.
Extended European Search Report for European Application No. 14861553.7, Search completed Jun. 8 2017, dated Jun. 19, 2017, 8 pgs.
Extended European Search Report for European Application No. 14863597.2, Search completed Jun. 6, 2017, dated Jun. 13, 2017, 9 pgs.
International Preliminary Report on Patentability for International Application No. PCT/AU2012/001441, dated May 27, 2014, 10 pgs.
International Search Report and Written Opinion for International Application No. PCT/AU2011/001127, date completed Nov. 11, 2011, dated Nov. 15, 2011, 13 pgs.
International Search Report and Written Opinion for International Application No. PCT/AU2012/001441, International Filing Date Nov. 23, 2012, Search Completed Feb. 26, 2013, dated Feb. 26, 2013, 14 pgs.
International Search Report and Written Opinion for International Application No. PCT/AU2014/001049, Search completed Feb. 10, 2015, dated Feb. 10, 2015, 8 pgs.
International Search Report and Written Opinion for International Application No. PCT/AU2014/050369, Search completed Feb. 20, 2015, dated Feb. 20, 2015, 14 pgs.
International Search Report and Written Opinion for International Application No. PCT/AU2015/050135, Search completed Jun. 30, 2015, dated Jun. 30, 2015, 26 pgs.

(56) References Cited

OTHER PUBLICATIONS

International Search Report and Written Opinion for International Application No. PCT/AU2015/050422, Search completed Oct. 14, 2015, dated Oct. 14, 2015, 17 pgs.
International Search Report and Written Opinion for International Application No. PCT/AU2015/050724, Search completed May 9, 2016, dated May 9, 2016, 8 pgs.
International Search Report and Written Opinion for International Application No. PCT/AU2015/050753, Search completed Feb. 10, 2016, dated Feb. 10, 2016, 10 pgs.
International Search Report and Written Opinion for International Application No. PCT/AU2015/050787, Search completed Mar. 16, 2016, dated Mar. 16, 2016, 10 pgs.
International Search Report and Written Opinion for International Application No. PCT/AU2016/050019, Search completed May 4, 2016, dated May 4, 2016, 16 pgs.
International Search Report and Written Opinion for International Application No. PCT/AU2015/050215, Search completed Jul. 30, 2015, dated Jul. 30, 2015, 8 pgs.
International Search Report for Australian Application 2011901829 Search Completed Feb. 6, 2012, dated Feb. 7, 2012, 3 pgs.
International Search Report for International Application No. PCT/AU2012/000511, International Filing Date May 11, 2012, Search Completed May 17, 2012, dated May 18, 2012, 4 pgs.
International Search Report for International Application No. PCT/AU2012/000512, International Filing Date May 11, 2012, Search Completed Jul. 10, 2012, dated Jul. 11, 2012, 4 pgs.
International Search Report for International Application No. PCT/AU2012/000513, International Filing Date May 11, 2012, Search Completed May 29, 2012, dated May 30, 2012, 5 pgs.
International Search Report for International Application No. PCT/AU2012/000515, International Filing Date May 11, 2012, Search Completed May 21, 2012, dated Jun. 4, 2012, 5 pgs.
International Search Report for International Application No. PCT/AU2012/000516, International Filing Date May 11, 2012, Search Completed Jul. 11, 2012, dated Jul. 12, 2012, 8 pgs.
International Search Report for International Application No. PCT/AU2012/000517, International Filing Date May 11, 2012, Search Completed Jun. 4, 2012, dated Jun. 6, 2012, 3 pgs.
International Search Report for International Application No. PCT/AU2012/000518, International Filing Date May 11, 2012, Search Completed Jun. 8, 2012, dated Jun. 12, 2012, 4 pgs.
Medtronic, Spinal Cord Stimulation, RestoreSensor Neurostimulator, Features and Specification: Specification, Printed Jun. 16, 2014, 2 pgs.
Medtronic, Spinal Cord Stimulation, RestoreSensor Neurostimulator, Features and Specification: Summary Printed Jun. 16, 2014, 1 pg.
Written Opinion for International Application No. PCT/AU2012/000511, International Filing Date May 11, 2012, Search Completed May 17, 2012, dated May 18, 2012, 5 pgs.
Written Opinion for International Application No. PCT/AU2012/000512, International Filing Date May 11, 2012, Search Completed Jul. 10, 2012, dated Jul. 11, 2012, 7 pgs.
Written Opinion for International Application No. PCT/AU2012/000513, International Filing Date May 11, 2012, Search Completed May 29, 2012, dated May 30, 2012, 10 pgs.
Written Opinion for International Application No. PCT/AU2012/000515, International Filing Date May 11, 2012, Search Completed May 21, 2012, dated Jun. 4, 2012, 4 pgs.
Written Opinion for International Application No. PCT/AU2012/000516, International Filing Date May 11, 2012, Search Completed Jul. 11, 2012, dated Jul. 12, 2012, 8 pgs.
Written Opinion for International Application No. PCT/AU2012/000517, International Filing Date May 11, 2012, Search Completed Jun. 4, 2012, dated Jun. 6, 2012, 5 pgs.
Written Opinion for International Application No. PCT/AU2012/000518, International Filing Date May 11, 2012, Search Completed Jun. 8, 2012, dated Jun. 12, 2012, 10 pgs.

Medtronic, RestoreSensor Neurostimulator, Retrieved from: http://web.archive.org/web/20150328092923/http://professional.medtronic.com:80/pt/neuro/scs/prod/restore-sensor/features-specifications/index.htm, Capture Date Jul. 9, 2012, Printed on May 11, 2017.
"Advanced Pain Therapy using Neurostimulation for Chronic Pain", Medtronic RestoreSensor clinical trial paper,Clinical summary, Nov. 2011, pp. 32.
"Battelle Neurotechnology—Moving Beyond the Limits in Neurotechnology", Battelle, www.battelle.org, May 2014, pp. 1-2.
"Haptic technology", Wikipedia, Retrieved from: http://en.wikipedia.org/wiki/Haptic_technology, Last modified on Sep. 15, 2014, Printed on Sep. 15, 2014, 5 pgs.
"Implants for surgery, Cardiac pacemakers", IS-1 standard ISO 5841-3-2000, Oct. 15, 2000.
"Neural Bypass Technology Enables Movement in Paralyzed Patient", Posted on Jul. 29, 2014, 6 a.m. in Brain chips/computer interface, pp. 1-2.
"Spinal Cord Stimulation, About Spinal Cord Stimulation", Medtronic, Retrieved from: http://professional.medtronic.com/pt/neuro/scs/edu/about/index.htm, Printed on Jun. 16, 2014, 2 pgs.
"Wide bandwidth BioAmplifier", http://www.psylab.com/html/default_bioamp.htm, Printed Jan. 30, 2014, 1-3 pages.
Andreassen, S. et al. "Muscle Fibre Conduction Velocity in Motor Units of the Human Anterior Tibial Muscle: a New Size Principle Parameter", J. Physiol, (1987), 391, pp. 561-571.
Andy, "Parafascicular-Center Median Nuclei Stimulation for Intractable Pain and Dyskinesia (Painful-Dyskinesia)", Stereotactic and Functional Neurosurgery, Appl. Neurophysiol., 43, No. 3-5, 1980, pp. 133-144.
Balzer et al., "Localization of cervical and cervicomedullary stimulation leads for pain treatment using median nerve somatosensay evoked potential collision testing", Journal of Neurosurgery, Jan. 2011, vol. 114, No. 1: pp. 200-205.
Blum, A. R., "An Electronic System for Extracelluar Neural Stimulation and Recording", Dissertation, Georgia Institute of Technology, Aug. 2007, Retrieved from http://smartech.gatech.edu/handle/1853/16192 on Jan. 30, 2012.
Borg et al., "Conduction velocity and refractory period of single motor nerve fibres in antecedent poliomyelitis", Journal of Neurology, Neurosurgery, and Psychiatry, vol. 50, 1987, 443-446.
Brown et al., "Impact of Deep Brain Stimulation on Upper Limb Askinesia in Parkinson's Disease", Annals of Neurology, 45, No. 4, 1999, pp. 473-488.
Budagavi et al., "Modelling of compound nerve action potentials health and disease", Engineering in Medicine and Biology Society, 1992 14th Annual International Conference of the IEEE. vol. 6. IEEE, 1992. pp. 2600-2601.
Coquery et al., "Backward and forward masking in the perception of cutaneous stimuli", Perception & Psychophysics, 1973, vol. 13.No. 2, pp. 161-163.
Dawson, G. D., "The relative excitability and conduction velocity of sensory and motor nerve fibres in man", Journal of Physiology, 1956, vol. 131(2), pp. 436-451.
Devergnas et al., A "Cortical potentials evoked by deep brain stimulation in the subthalamic area", Front Syst Neurosci. 2011; 5: 30. May 13, 2011.doi:10.3389/fnsys.2011.00030.
Dijkstra, E. A., "Ultrasonic Distance Detection for a Closed-Loop Spinal Cord Stimulation System", Proceedings—19th International Conference—IEEE/EMBS Oct. 30-Nov. 2, 1997, Chicago, IL. 4 pgs.
Schmidt et al., "Gating of tactile input from the hand", Exp Brain Res, 1990, 79, pp. 97-102.
Siegfried et al., "Bilateral Chronic Electrostimulation of Ventroposterolateral Pallidum: A New Therapeutic Approach for Alleviating all Parkinsonian Symptoms", Neurosurgery, 35, No. 6, Dec. 1994, pp. 1126-1130.
Siegfried et al., "Intracerebral Electrode Implantation System", Journal of Neurosurgery, vol. 59, No. 2, Aug. 1983, pp. 356-3591.
Srinivasan, S, "Electrode/Electrolyte Interfaces: Structure and Kinetics of Charge Transfer", Fuel Cells, 2006, Chapter 2, 67 Pages.

(56) References Cited

OTHER PUBLICATIONS

Struijk et al, "Paresthesia Thresholds in Spinal Cord Stimulation: A Comparison of Theoretical Results with Clinical Data", IEEE Transactions on Rehabilitation Engineering, vol. 1, No. 2, Jun. 1993, pp. 101-108.
Sufka et al., "Gate Control Theory Reconsidered", Brain and Mind, 3, No. 2, 2002, pp. 277-290.
Tamura et al., "Increased Nodal Persistent Na+ Currents in Human Neuropathy and Motor Neuron Disease Estimated by Latent Addition", Clinical Neurophysiology 117, No. 11 (Nov. 2006): 2451-2458, doi:10.1016/j.clinph.2006.07.309.
Tasker, "Deep Brain Stimulation is Preferable to Thalamotomy for Tremor Suppression", Surgical Neurology, 49, No. 2, 1998, pp. 145-153.
Taylor et al., "Spinal Cord Stimulation for Chronic Back and Leg Pain and Failed Back Surgery Syndrome: A Systematic Review and Analysis of Prognostic Factors", SPINE, vol. 30, No. 1, 2004, pp. 152-160.
Tomas et al., "Dorsal Root Entry Zone (DREZ) Localization Using Direct Spinal Cord Stimulation Can Improve Results of the Drez Thermocoagulation Procedure for Intractable Pain Relief", Pain, 2005, vol. 116, pp. 159-163.
Tscherter et al., "Spatiotemporal Characterization of Rhythmic Activity in Rat Spinal Cord Slice Cultures", European Journal of Neuroscience 14, No. 2 (2001), pp. 179-190.
Villavicencio, Alan T., "Laminectomy versus Percutaneous Electrode Placement for Spinal Cord Stimulation," Neurosurgery, vol. 46 (2), Feb. 2000, pp. 399-405.
Woessner, "Blocking Out the Pain, Electric Nerve Block Treatments for Sciatic Neuritis", Retrieved from: http://www.practicalpainmanagement.com/pain/spine/radiculopathy/blocking-out-pain, Last updated Jan. 10, 2012.
Wolter et al., "Effects of sub-perception threshold spinal cord stimulation in neuropathic pain: A randomized controlled double-blind crossover study", European Federation of International Association for the Study of Pain Chapters, 2012, pp. 648-655.
Wu et al., "Changes in Aβ Non-nociceptive Primary Sensory Neurons in a Rat Model of Osteoarthritis Pain", Molecular Pain 6, No. 1 (Jul. 1, 2010): 37, doi:10.1186/1744-8069-6-37.
Xie et al., "Functional Changes in Dorsal Root Ganglion Cells after Chronic Nerve Constriction in the Rat", Journal of Neurophysiology 73, No. 5 (May 1, 1995): 1811-1820.
Xie et al., "Sinusoidal Time-Frequency Wavelet Family and its Application in Electrograstrographic Signal Analysis", Proceedings of the 20th Annual International Conference of the IEEE Engineering in Medicine and Biology Society, vol. 20, No. 3, Oct. 29, 1998, pp. 1450-1453.
Yearwood, T. L., "Pulse Width Programming in Spinal Cord Stimulation: a Clinical Study", Pain Physician. 2010. vol. 13, pp. 321-335.
Yingling et al., "Use of Antidromic Evoked Potentials in Placement of Dorsal Cord Disc Electrodes", Applied Neurophysiology, 1986, vol. 49, pp. 36-41.
Yuan, S. et al., "Recording monophasic action potentials using a platinum-electrode ablation catheter", Europace. Oct. 2000; 2(4):312-319.
Dillier, N. et al., "Measurement of the electrically evoked compound action potential via a neural response telemetry system", Ann. Otol. Rhinol. Laryngol., vol. 111, No. 5, May 2002, pp. 407-414.
Doiron et al., "Persistent Na+ Current Modifies Burst Discharge by Regulating Conditional Backpropagation of Dendritic Spikes", Journal of Neurophysiology 89, No. 1 (Jan. 1, 2003): 324-337, doi:10.1152/jn.00729.2002.
England et al., "Increased Numbers of Sodium Channels Form Along Demyelinated Axons", Brain Research 548, No. 1-2 (May 10, 1991): 334-337.
Fagius, J. et al., "Sympathetic Reflex Latencies and Conduction Velocities in Normal Man", Journal of Neurological Sciences, 1980. vol. 47, pp. 433-448.

Falowski et al., "Spinal Cord Stimulation: an update", Neurotherapeutics: The Journal of the American Society for Experimental NeuroTherapeutics 5, No. 1, Jan. 2008, pp. 86-99.
Franke et al., FELIX "An Online Spike Detection and Spike Classification Algorithm Capable of Instantaneous Resolution of Overlapping Spikes", Journal of Computational Neuroscience, 2010, vol. 29, No. 1-2, pp. 127-148.
Fuentes et al., "Spinal Cord Stimulation Restores Locomotion in Animal Models of Parkinson's Disease", Science, vol. 323, No. 5921, Mar. 20, 2009, pp. 1578-1582.
George et al., "Vagus nerve stimulation: a new tool for brain research and therapy", Biological Psychiatry 47, No. 4, Feb. 15, 2000, pp. 287-295.
Goodall, E. V., "Modeling Study of Activation and Propagation delays During Stimulation of Peripheral Nerve Fibres with a Tripolar Cuff Electrode", IEEE Transactions on Rehabilitation Engineering, vol. 3, No. 3, Sep. 1995, pp. 272-282.
Gorman et al., "ECAP Mapping of the Spinal Cord: Influence of Electrode Position on Aβ Recruitment", (2012), In 16th Annual Meeting. Presented at the North American Neuromodulation Society, Las Vegas, NV.
Gorman et al., "Neural Recordings for Feedback Control of Spinal Cord Stimulation: Reduction of Paresthesia Variability." 2013, In International Neuromodulation Society 11th World Congress. Presented at the International Neuromodulation Society 11th World Congress, Berlin, Germany.
Hallstrom et al, "Distribution of lumbar spinal evoked potentials and their correlation with stimulation-induced paresthesiae" (1991), Electroencephalography and clinical neurophysiology 80:126-139.
Harper, A. A. et al., "Conduction Velocity is Related to Morphological Cell Type in Rat Dorsal Root Ganglion Neurones", J. Physiol, (1985), 359, pp. 31-46.
Holsheimer et al., "Optimum Electrode Geometry for Spinal Cord Stimulation: the Narrow Bipole and Tripole", Medical and Biological Engineering and Computing, 35, No. 5, 1997, pp. 493-497.
Huff, Terry B. et al., "Real-Time CARS Imaging Reveals a Calpain-Dependent Pathway for Paranodal Myelin Retraction during High-Frequency Stimulation", PLoS ONE vol. 6, issue 3 (Mar. 3, 2011): e17176, 11 pgs.
Hui, Ouyang et al., "Compression Induces Acute Demyelination and Potassium Channel Exposure in Spinal Cord", Journal of Neurotrauma 27, No. 6, Jun. 2010, 1109-1120, doi:10.1089/neu.2010.1271.
Kent et al., "Instrumentation to Record Evoked Potentials for Closed-Loop Control of Deep Brain Stimulation", Conf. Proc. IEEE Eng. Med Biol. Sol, Aug. 2012, 10 pgs.
Kent et al., AR "Recording evoked potentials during deep brain stimulation: development and validation of instrumentation to suppress the stimulus artefact", J Neural Eng. Jun. 2012; 9 (3):036004, Apr. 18, 2012. doi: 10.1088/1741-2560/9/3/036004.
Kim et al., "A Wavelet-Based Method for Action Potential Detection From Extracellular Neural Signal Recording With Low Signal-to-Noise Ratio", IEEE Transactions on Biomedical Engineering, vol. 50. No. 8, Aug. 2003.
Kim et al., "Cell Type-specific Changes of the Membrane Properties of Peripherally-axotomized Dorsal Root Ganglion Neurons in a Rat Model of Neuropathic Pain", Neuroscience 86, No. 1 (May 21, 1998): 301-309, doi:10.1016/S0306-4522(98)00022-0.
Krames et al., "Neuromodulation", 1st Edition, Academic Press, 2009, p. 540-541.
Krarup, Christian "Compound sensory action potential in normal and pathological human nerves", Muscle & nerve, vol. 29, No. 4 (2004), pp. 465-483.
Krishnan et al., "Excitability Differences in Lower-Limb Motor Axons During and After Ischemia", Muscle & nerve, vol. 31, No. 2 (2005), pp. 205-213.
Kumar et al., "Deep Brain Stimulation for Intractable Pain: a 15-year Experience", Neurosurgery, Issue 40, No. 4, Apr. 1997, pp. 736-747.
Kumar et al., "Double-blind evaluation of subthalamic nucleus deep brain stimulation in advanced Parkinson's disease", by the American Academy of Neurology, 51, No. 3, Sep. 1, 1998, pp. 850-855.

(56) References Cited

OTHER PUBLICATIONS

Kumar et al., "Globus Pallidus Deep Brain Stimulation for Generalized Dystonia: Clinical and Pet Investigation", Neurology, 53, No. 4, 1999, pp. 871-874.
Laird et al., "A Model of Evoked Potentials in Spinal Cord Stimulation", IEEE Engineering in Medicine & Biology Society, 35th Annual Conference. Osaka, Japan: Jul. 3-7, 2013, pp. 6555-6558.
Lempka, Scott, "The Electrode-Tissue Interface During Recording and Stimulation in the Central Nervous System", published on May, 2010.
Levy et al., "Incidence and Avoidance of Neurologic Complications with Paddle Type Spinal Cord Stimulation Leads", Neuromodulation 14(15), Sep. 2011, pp. 412-22.
Li et al., S, "Resonant antidromic cortical circuit activation as a consequence of high-frequency subthalamic deep-brain stimulation", J Neurophysiol. Dec. 2007; 98(6): 3525-37. First published Oct. 10, 2007. doi:10.1152/jn.00808.2007.
Ma et al., "Similar Electrophysiological Changes in Axotomized and Neighboring Intact Dorsal Root Ganglion Neurons", Journal of Neurophysiology 89, No. 3 (Mar. 1, 2003): 1588-1602, doi:10.1152/jn.00855.2002.
Macefield, "Spontaneous and Evoked Ectopic Discharges Recorded from Single Human Axons", Muscle & Nerve 21, No. 4, Apr. 1998, pp. 461-468.
Mahnam, A et al., "Measurement of the current-distance relationship using a novel refractory interaction technique", J. Neural Eng. 6 (2009), pp. 036005 (published May 20, 2009) Abstract, Sec. 2.2 & Figure 2b, 036005.
Massachusetts Institute of Techn, "The Compound Action Potential of the Frog Sciatic Nerve", Quantitative Physiology: Cells and Tissues. Fall, 1999, Retrieved from http://umech.mit.edu/freeman/6.021J/2001/1ab.pdf on May 22, 2012.
Matzner et al., "Na+ Conductance and the Threshold for Repetitive Neuronal Firing", Brain Research 597, No. 1 (Nov. 27, 1992): 92-98, doi:10.1016/0006-8993(92)91509-D.
McGill, Kevin et al., "On the Nature and Elimination of Stimulus Artifact in Nerve Signals Evoked and Recorded Using Surface Electrodes", IEEE Transactions on Biomedical Engineering, vol. BME-29, No. 2, Feb. 1982, pp. 129-137.
Melzack et al., "Pain mechanisms: a new theory", Science, New York, New York, vol. 150, No. 3699, Nov. 19, 1965, pp. 971-979.
Miles et al., "An Electrode for Prolonged Stimulation of the Brain", Proc. 8th Meeting World Soc. Stereotactic and Functional Neurosurgery, Part III, Zurich, 1981, Appl. Neurophysiol, 45, 1982, pp. 449-445 1982.
Misawa et al., "Neuropathic Pain Is Associated with Increased Nodal Persistent Na(+) Currents in Human Diabetic Neuropathy", Journal of the Peripheral Nervous System: Jpns, 14, No. 4 (Dec. 2009): 279-284.
Nordin et al., "Ectopic Sensory Discharges and Paresthesiae in Patients with Disorders of Peripheral Nerves, Dorsal Roots and Dorsal Columns", Pain 20, No. 3 (Nov. 1984): 231-245, doi: 10.1016/0304-3959(84)90013-7.
Oakley et al., "Spinal Cord Stimulation: Mechanisms of Action", Spine 27, No. 22, Nov. 15, 2002, pp. 2574-2583.
Oakley et al., "Transverse Tripolar Spinal Cord Stimulation: Results of an International Multicenter Study", Neuromodulation, vol. 9, No. 3, 2006, pp. 192-203.
Obradovic et al., "Effect of pressure on the spinal cord during spinal cord stimulation in an animal model", Poster, 18th Annual Meeting of the North American Neuromodulation Society, Dec. 11-14, 2014, Las Vegas.
Oh et al., "Long-term hardware-related complications of deep brain stimulation", Neurosurgery, vol. 50, No. 6, Jun. 2002, pp. 1268-1274, discussion pp. 1274-1276.
Opsommer, E. et al., "Determination of Nerve Conduction Velocity of C-fibres in Humans from Thermal Thresholds to Contact Heat (Thermode) and from Evoked Brain Potentials to Radiant Heat (CO2 Laser)", Neurophysiologie Clinique 1999, vol. 29, pp. 411-422.
Orstavik, Kristin et al., "Pathological C-fibres in patients with a chronic painful condition", Brain (2003), 126, 567-578.
Parker et al., "Closing the Loop in Neuromodulation Therapies: Spinal Cord Evoked Compound Action Potentials During Stimulation for Pain Management (230)." 2011, In 15th Annual Meeting, North American Neuromodulation Society (p. 48). Presented at the North American Neuromodulation Society, Las Vegas.
Parker et al., "Compound action potentials recorded in the human spinal cord during neurostimulation for pain relief", Pain, 2012, vol. 153, pp. 593-601.
Parker et al., "Electrically Evoked Compound Action Potentials Recorded From the Sheep Spinal Cord", Neuromodulation, vol. 16, 2013, pp. 295-303.
Penar et al., "Cortical Evoked Potentials Used for Placement of a Laminotomy Lead Array: A Case Report", Neuromodulation: Technology at the Neural Interface, accessed Apr. 19, 2011, doi:10.1111/j.1525-1403.2011.00352.x.
Richter et al., "EMG and SSEP Monitoring During Cervical Spinal Cord Stimulation", Journal of Neurosurgical Review 2011, Southern Academic Press, 1(S1), 2011, pp. 61-63.
Ridder et al., "Burst Spinal Cord Stimulation for Limb and Back Pain", World Neurosurgery, 2013, 9 pgs.
Ridder et al., "Burst Spinal Cord Stimulation toward Paresthesia-Free Pain Suppression", May 2010, vol. 66, pp. 986-990.
Roy, S. H. et al., "Effects of Electrode Location on Myoelectric Conduction Velocity and Median Frequency Estimates", J. Appl. Physiol. 61 (4), 1986, pp. 1510-1517.
Extended European Search Report for European Application No. 15768956.3, Search completed Oct. 3, 2017, dated Oct. 10, 2017, 8 Pgs.
Al-Ani et al., "Automatic removal of high-amplitude stimulus artefact from neuronal signal recorded in the subthalamic nucleus", Journal of Neuroscience Methods, vol. 198, Issue 1, 2011, pp. 135-146.
Extended European Search Report for European Application No. 16739680.3, Search completed Jun. 1, 2018, dated Jun. 12, 2018, 9 Pgs.
French et al., "Information transmission at 500 bits/s by action potentials in a mechanosensory neuron of the cockroach", Neuroscience Letters, vol. 243, No. 1-3, Feb. 1, 1998, pp. 113-116.
Herreras, "Local Field Potentials: Myths and Misunderstandings", Frontiers in Neural Circuits, Dec. 15, 2016, vol. 10, Article 1101, 16 pgs.
Extended European Search Report for European Application No. 16802238.2, Search completed Oct. 17, 2018, dated Oct. 24, 2018, 8 Pgs.
Partial European Search Report for European Application No. 16775966.1, Search completed Oct. 26, 2018, dated Nov. 6, 2018, 11 Pgs.
He et al., "Perception threshold and electrode position for spinal cord stimulation", Pain, 59 (1994) 55-63 pages.
Holsheimer et al., "Significance of the Spinal Cord Position in Spinal Cord Stimulation", Acta Neurochir (1995) [Suppl] 64: 119-124 pages.
Holsheimer et al., "Spinal Geometry and Paresthesia Coverage in Spinal Cord Stimulation", (1998 paper) 8 Pages.
Olin et al., "Postural Changes in Spinal Cord Stimulation Perceptual Thresholds", Neuromodulation, vol. 1 , No. 4, 1998, pp. 171-175.
Rattay, "Analysis of Models for External Stimulation of Axons", IEEE Transactions on Biomedical Engineering, vol. BME-33, No. 10, Oct. 1986, pp. 974-977.
Ross et al., "Improving Patient Experience with Spinal Cord Stimulation: Implications of Position-Related Changes in Neurostimulation", Neuromodulation 2011; e-pub ahead of print. DOI: 10.1111/j.1525-1403.2011.00407.x 6 pages.
Struijk, "The Extracellular Potential of a Myelinated Nerve Fiber in an Unbounded Medium and in Nerve Cuff Models", Biophysical Journal vol. 72 Jun. 1997 2457-2469.

METHOD AND SYSTEM FOR CONTROLLING ELECTRICAL CONDITIONS OF TISSUE

CROSS-REFERENCE TO RELATED APPLICATIONS

This application is the National Stage of International Application No. PCT/AU2013/001279 filed Nov. 6, 2013, which claims the benefit of Australian Provisional Patent Application No. 2012904836 filed Nov. 6, 2012, and Australian Provisional Patent Application No. 2012904838 filed Nov. 6, 2012, which are incorporated herein by reference.

TECHNICAL FIELD

The present invention relates to controlling the electrical conditions of tissue, for example for use in suppressing artefact to enable improved measurement of a response to a stimulus, such as measurement of a compound action potential by using one or more electrodes implanted proximal to a neural pathway.

BACKGROUND OF THE INVENTION

Neuromodulation is used to treat a variety of disorders including chronic pain, Parkinson's disease, and migraine. A neuromodulation system applies an electrical pulse to tissue in order to generate a therapeutic effect. When used to relieve chronic pain, the electrical pulse is applied to the dorsal column (DC) of the spinal cord or dorsal root ganglion (DRG). Such a system typically comprises an implanted electrical pulse generator, and a power source such as a battery that may be rechargeable by transcutaneous inductive transfer. An electrode array is connected to the pulse generator, and is positioned in the dorsal epidural space above the dorsal column. An electrical pulse applied to the dorsal column by an electrode causes the depolarisation of neurons, and generation of propagating action potentials. The fibres being stimulated in this way inhibit the transmission of pain from that segment in the spinal cord to the brain.

While the clinical effect of spinal cord stimulation (SCS) is well established, the precise mechanisms involved are poorly understood. The DC is the target of the electrical stimulation, as it contains the afferent AP fibres of interest. Aβ fibres mediate sensations of touch, vibration and pressure from the skin. The prevailing view is that SCS stimulates only a small number of Aβ fibres in the DC. The pain relief mechanisms of SCS are thought to include evoked antidromic activity of Aβ fibres having an inhibitory effect, and evoked orthodromic activity of Aβ fibres playing a role in pain suppression. It is also thought that SCS recruits Aβ nerve fibres primarily in the DC, with antidromic propagation of the evoked response from the DC into the dorsal horn thought to synapse to wide dynamic range neurons in an inhibitory manner.

Neuromodulation may also be used to stimulate efferent fibres, for example to induce motor functions. In general, the electrical stimulus generated in a neuromodulation system triggers a neural action potential which then has either an inhibitory or excitatory effect. Inhibitory effects can be used to modulate an undesired process such as the transmission of pain, or to cause a desired effect such as the contraction of a muscle.

The action potentials generated among a large number of fibres sum to form a compound action potential (CAP). The CAP is the sum of responses from a large number of single fibre action potentials. The CAP recorded is the result of a large number of different fibres depolarising. The propagation velocity is determined largely by the fibre diameter and for large myelinated fibres as found in the dorsal root entry zone (DREZ) and nearby dorsal column the velocity can be over 60 ms$^{-1}$. The CAP generated from the firing of a group of similar fibres is measured as a positive peak potential P1, then a negative peak N1, followed by a second positive peak P2. This is caused by the region of activation passing the recording electrode as the action potentials propagate along the individual fibres.

To better understand the effects of neuromodulation and/or other neural stimuli, it is desirable to record a CAP resulting from the stimulus. However, this can be a difficult task as an observed CAP signal will typically have a maximum amplitude in the range of microvolts, whereas a stimulus applied to evoke the CAP is typically several volts. Electrode artefact usually results from the stimulus, and manifests as a decaying output of several millivolts throughout the time that the CAP occurs, presenting a significant obstacle to isolating the CAP of interest. Some neuromodulators use monophasic pulses and have capacitors to ensure there is no DC flow to the tissue. In such a design, current flows through the electrodes at all times, either stimulation current or equilibration current, hindering spinal cord potential (SCP) measurement attempts. The capacitor recovers charge at the highest rate immediately after the stimulus, undesirably causing greatest artefact at the same time that the evoked response occurs.

To resolve a 10 uV SCP with 1 uV resolution in the presence of an input 5V stimulus, for example, requires an amplifier with a dynamic range of 134 dB, which is impractical in implant systems. As the neural response can be contemporaneous with the stimulus and/or the stimulus artefact, CAP measurements present a difficult challenge of amplifier design. In practice, many non-ideal aspects of a circuit lead to artefact, and as these mostly have a decaying exponential appearance that can be of positive or negative polarity, their identification and elimination can be laborious.

A number of approaches have been proposed for recording a CAP. King (U.S. Pat. No. 5,913,882) measures the spinal cord potential (SCP) using electrodes which are physically spaced apart from the stimulus site. To avoid amplifier saturation during the stimulus artefact period, recording starts at least 1-2.5 ms after the stimulus. At typical neural conduction velocities, this requires that the measurement electrodes be spaced around 10 cm or more away from the stimulus site, which is undesirable as the measurement then necessarily occurs in a different spinal segment and may be of reduced amplitude.

Nygard (U.S. Pat. No. 5,785,651) measures the evoked CAP upon an auditory nerve in the cochlea, and aims to deal with artefacts by a sequence which comprises: (1) equilibrating electrodes by short circuiting stimulus electrodes and a sense electrode to each other; (2) applying a stimulus via the stimulus electrodes, with the sense electrode being open circuited from both the stimulus electrodes and from the measurement circuitry; (3) a delay, in which the stimulus electrodes are switched to open circuit and the sense electrode remains open circuited; and (4) measuring, by switching the sense electrode into the measurement circuitry. Nygard also teaches a method of nulling the amplifier following the stimulus. This sets a bias point for the amplifier during the period following stimulus, when the electrode is not in equilibrium. As the bias point is reset each cycle, it is susceptible to noise. The Nygard measurement amplifier is a differentiator during the nulling phase which makes it susceptible to pickup from noise and input transients when a non-ideal amplifier with finite gain and bandwidth is used for implementation.

Daly (US Patent Application No. 2007/0225767) utilizes a biphasic stimulus plus a third phase "compensatory" stimulus which is refined via feedback to counter stimulus artefact. As for Nygard, Daly's focus is the cochlea. Daly's measurement sequence comprises (1) a quiescent phase where stimulus and sense electrodes are switched to Vdd; (2) applying the stimulus and then the compensatory phase, while the sense electrodes are open circuited from both the stimulus electrodes and from the measurement circuitry; 3) a load settling phase of about 1 μs in which the stimulus electrodes and sense electrodes are shorted to Vdd; and (4) measurement, with stimulus electrodes open circuited from Vdd and from the current source, and with sense electrodes switched to the measurement circuitry. However a 1 μs load settling period is too short for equilibration of electrodes which typically have a time constant of around 100 μs. Further, connecting the sense electrodes to Vdd pushes charge onto the sense electrodes, exacerbating the very problem the circuit is designed to address.

Evoked responses are less difficult to detect when they appear later in time than the artefact, or when the signal-to-noise ratio is sufficiently high. The artefact is often restricted to a time of 1-2 ms after the stimulus and so, provided the neural response is detected after this time window, data can be obtained. This is the case in surgical monitoring where there are large distances between the stimulating and recording electrodes so that the propagation time from the stimulus site to the recording electrodes exceeds 2 ms.

Because of the unique anatomy and tighter coupling in the cochlea, cochlear implants use small stimulation currents relative to the tens of mA sometimes required for SCS, and thus measured signals in cochlear systems present a relatively lower artefact. To characterize the responses from the dorsal columns, high stimulation currents and close proximity between electrodes are required. Moreover, when using closely spaced electrodes both for stimulus and for measurement the measurement process must overcome artefact directly, in contrast to existing "surgical monitoring" techniques involving measurement electrode(s) which are relatively distant from the stimulus electrode(s).

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood that the element may be any one of the listed options, or may be any combination of two or more of the listed options.

SUMMARY OF THE INVENTION

According to a first aspect the present invention provides a method for controlling electrical conditions of tissue, the method comprising:

providing a plurality of electrodes including at least one nominal feedback sense electrode and at least one nominal compensation electrode, the electrodes being positioned proximal to the tissue and being in electrical contact with the tissue;

connecting a feedback signal from the feedback sense electrode to an input of a feedback amplifier, and referencing the amplifier to a desired electrical value; and connecting an output of the feedback amplifier to the compensation electrode such that the feedback amplifier drives the tissue via the compensation electrode in a feedback arrangement which seeks to drive the feedback signal to the desired electrical value.

According to a second aspect the present invention provides a method for measuring a neural response to a stimulus, the method comprising:

providing a plurality of electrodes including at least one nominal stimulus electrode, at least one nominal measurement electrode, at least one nominal feedback sense electrode and at least one nominal compensation electrode, the electrodes being positioned proximal to neural tissue and being in electrical contact with the tissue;

applying an electrical stimulus to the neural tissue from the stimulus electrode;

connecting a feedback signal from the feedback sense electrode to an input of a feedback amplifier, and referencing the amplifier to a desired electrical value;

connecting an output of the feedback amplifier to the compensation electrode such that the feedback amplifier drives the neural tissue via the compensation electrode in a feedback arrangement which seeks to drive the neural tissue to the desired electrical value; and obtaining a measurement of a neural response from the measurement electrode.

According to a third aspect the present invention provides an implantable device for controlling electrical conditions of tissue, the device comprising:

a plurality of electrodes including at least one nominal feedback sense electrode and at least one nominal compensation electrode, the electrodes being configured to be positioned proximal to the tissue to make electrical contact with the tissue;

a feedback amplifier configured to be referenced to a desired electrical value and to take as an input a feedback signal from the feedback sense electrode, an output of the feedback amplifier being connected to the compensation electrode such that the feedback amplifier is configured to drive the neural tissue via the compensation electrode in a feedback arrangement which seeks to drive the feedback signal to the desired electrical value.

In some embodiments the device of the third aspect may be further configured for measuring a neural response to a stimulus, and may further comprise: one or more nominal stimulus electrodes; one or more nominal sense electrodes; a stimulus source for providing a stimulus to be delivered from the one or more stimulus electrodes to neural tissue; measurement circuitry for amplifying a neural signal sensed at the one or more sense electrodes; and a control unit configured to apply an electrical stimulus to the neural tissue from the stimulus electrode and obtain a measurement of a neural response from the measurement electrode.

In some embodiments of the second and third aspects of the invention the feedback amplifier may be disconnected during application of a neural stimulus by disconnecting the feedback sense electrode from the feedback amplifier and/or by disconnecting an output of the feedback amplifier from the compensation electrode. Alternatively, during application of the neural stimulus, for example during the entire period of stimulation, the feedback amplifier may operate and be in connection with the feedback sense electrode and compensation electrode.

In preferred embodiments, the feedback sense electrode and the measurement electrode are located outside the dipole formed by the stimulus electrode and the compensating electrode. In such embodiments the operation of the feedback amplifier acts to spatially shield the measurement electrode from the stimulus field, noting that the voltage at points between the poles of a dipole is comparable to the voltage on the electrodes, whereas outside the dipole the voltage drops with the square of distance.

Preferred embodiments of the invention may thus reduce artefact by reducing interaction between the stimulus and the measurement recording via a measurement amplifier input capacitance.

Some embodiments of the invention may utilise a blanking circuit for blanking the measurement amplifier during and/or close in time to the application of a stimulus. However, alternative embodiments may utilise an unblanked measurement amplifier, which connects a measurement electrode to an analog-to-digital circuit, significantly reducing complexity in the measurement signal chain.

The desired electrical value may be zero voltage, i.e. electrical ground. The electrical ground may be referenced to a patient ground electrode distal from the array such as a device body electrode, or to a device ground. Driving the feedback signal to ground will thus act to counteract any non-zero stimulus artefact produced by application of the stimulus.

In alternative embodiments a non-zero voltage may in some circumstances be desired in the tissue and the feedback amplifier may thus be referenced to a non-zero electrical value in such embodiments.

The electrodes are preferably part of a single electrode array, and are physically substantially identical whereby any electrode of the array may serve as any one of the nominal electrodes at a given time. Alternatively the electrodes may be separately formed, and not in a single array, while being individually positioned proximal to the tissue of interest.

In preferred embodiments of the invention, the feedback sense electrode, compensation electrode, stimulus electrode and sense electrode are selected from an implanted electrode array. The electrode array may for example comprise a linear array of electrodes arranged in a single column along the array. Alternatively the electrode array may comprise a two dimensional array having two or more columns of electrodes arranged along the array. Preferably, each electrode of the electrode array is provided with an associated measurement amplifier, to avoid the need to switch the sense electrode(s) to a shared measurement amplifier, as such switching can add to measurement artefact. Providing a dedicated measurement amplifier for each sense electrode is further advantageous in permitting recordings to be obtained from multiple sense electrodes simultaneously.

In the first through third aspects of the invention, the measurement may be a single-ended measurement obtained by passing a signal from a single sense electrode to a single-ended amplifier. Alternatively, the measurement may be a differential measurement obtained by passing signals from two measurement electrodes to a differential amplifier. A single stimulus electrode may apply monopolar stimulus referenced to a distal reference point such as an implant case body, alternatively two stimulus electrodes may be used to apply bipolar stimuli, or three stimulus electrodes may be used to apply a tripolar stimulus for example using on stimulus electrode as a cathode and two stimulus electrodes as anodes, and vice versa. The stimulus may be monophasic, biphasic, or otherwise.

Embodiments of the invention may prove beneficial in obtaining a CAP measurement which has lower dynamic range and simpler morphology as compared to systems more susceptible to artefact. Such embodiments of the present invention may thus reduce the dynamic range requirements of implanted amplifiers, and may avoid or reduce the complexity of signal processing systems for feature extraction, simplifying and miniaturizing an implanted integrated circuit. Such embodiments may thus be particularly applicable for an automated implanted evoked response feedback system for stimulus control.

According to another aspect the present invention provides a computer program product comprising computer program code means to make an implanted processor execute a procedure for controlling electrical conditions of neural tissue, the computer program product comprising computer program code means for carrying out the method of the first or second aspect.

According to a further aspect the present invention provides a computer readable storage medium, excluding signals, loaded with computer program code means to make an implanted processor execute a procedure for controlling electrical conditions of neural tissue, the computer readable storage medium loaded with computer program code means for carrying out the method of the first or second aspect.

The present invention recognises that when considering spinal cord stimulation, obtaining information about the activity within the spinal segment where stimulation is occurring is highly desirable. Observing the activity and extent of propagation both above (rostrally of) and below (caudally of) the level of stimulation is also highly desirable. The present invention recognises that in order to record the evoked activity within the same spinal segment as the stimulus requires an evoked potential recording system which is capable of recording an SCP within approximately 3 cm of its source, i.e. within approximately 0.3 ms of the stimulus, and further recognises that in order to record the evoked activity using the same electrode array as applied the stimulus requires an evoked potential recording system which is capable of recording an SCP within approximately 7 cm of its source, i.e. within approximately 0.7 ms of the stimulus.

In some embodiments the method of the present invention may be applied to measurement of other bioelectrical signals, such as muscle potentials. The method of the present invention may be applicable to any measurement of any voltage within tissue during or after stimulation, and where the stimulation may obscure the voltage being measured. Such situations include the measurement of evoked spinal cord potentials, potentials evoked local to an electrode during deep brain stimulation (DBS), the measurement of EEGs during deep brain stimulation (where the source of the potential is distant from the stimulating electrodes), the measurement of signals in the heart (ECGs) by a pacemaker, the measurement of voltages in stimulated muscles (EMGs), and the measurement of EMGs triggered by the stimulation of distant and controlling nervous tissue.

BRIEF DESCRIPTION OF THE DRAWINGS

An example of the invention will now be described with reference to the accompanying drawings, in which:

FIG. 11a plots the measurements from an electrode array in response to a stimulus delivered by the array to a sheep dorsal column, while

DESCRIPTION OF THE PREFERRED EMBODIMENTS

Figure 1:
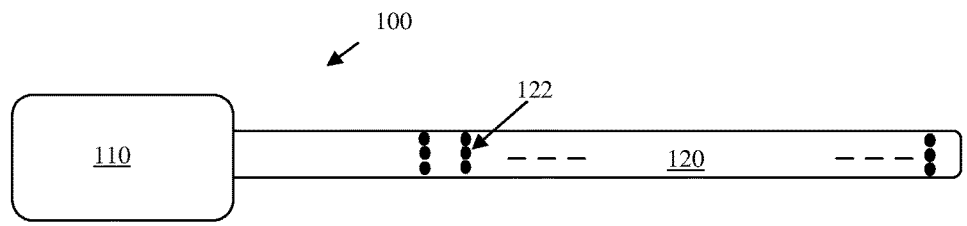
FIG. 1 illustrates an implantable device suitable for implementing the present invention.

FIG. 1 illustrates an implantable device 100 suitable for implementing the present invention. Device 100 comprises an implanted control unit 110, which controls application of a sequence of neural stimuli. In this embodiment the unit 110 is also configured to control a measurement process for obtaining a measurement of a neural response evoked by a single stimulus delivered by one or more of the electrodes 122. Device 100 further comprises an electrode array 120 consisting of a three by eight array of electrodes 122, each of which may be selectively used as the stimulus electrode, sense electrode, compensation electrode or sense electrode.

Figure 2:
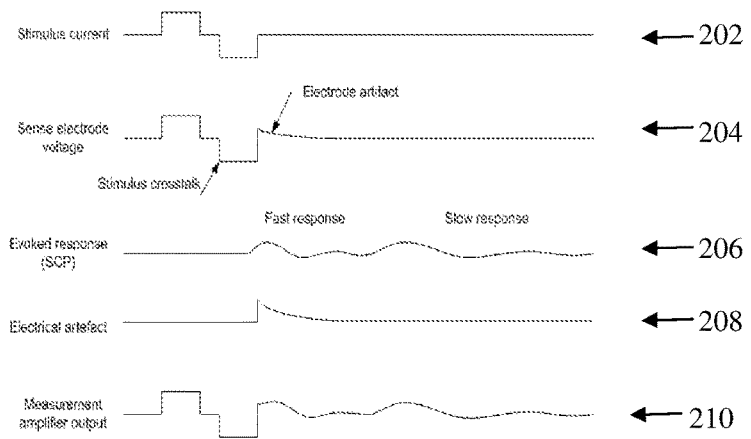
FIG. 2 illustrates currents and voltages which can contribute to SCP measurements.
Figure 3:
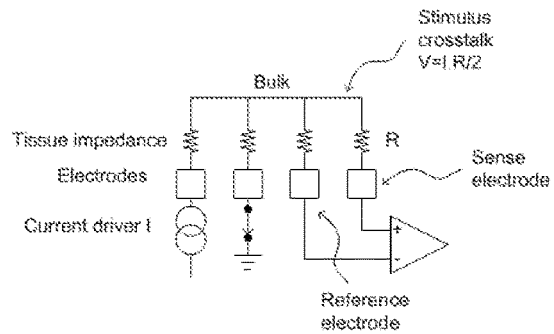
FIG. 3 illustrates the equivalent circuit of a typical system for applying a neural stimulus and attempting to measure a neural response.

FIG. 2 shows the currents and voltages that contribute to spinal cord potential (SCP) measurements in a typical system of the type shown in FIG. 3. These signals include the stimulus current 202 applied by two stimulus electrodes, which is a charge-balanced biphasic pulse to avoid net charge transfer to or from the tissue and to provide low artefact. Alternative embodiments may instead use three electrodes to apply a tripolar charge balanced stimulus for example where a central electrode. In the case of spinal cord stimulation, the stimulus currents 202 used to provide paraesthesia and pain relief typically consist of pulses in the range of 3-30 mA amplitude, with pulse width typically in the range of 100-400 μs, or alternatively may be paraesthesia-free such as neuro or escalator style stimuli. The stimuli can comprise monophasic or biphasic pulses.

The stimulus 202 induces a voltage on adjacent electrodes, referred to as stimulus crosstalk 204. Where the stimuli 202 are SCP stimuli they typically induce a voltage 204 in the range of about 1-5 V on a SCP sense electrode.

Figure 4:
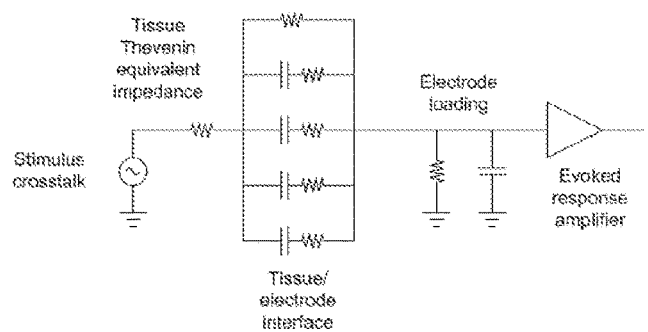
FIG. 4 is an equivalent circuit modelling the tissue/electrode interface and electrode loading.

The stimulus 202 also induces electrode artefact. The mechanism of artefact production can be considered as follows. The stimulus crosstalk can be modelled as a voltage, with an equivalent output impedance. In a human spinal cord, this impedance is typically around 500 ohms per electrode, but will be larger or smaller in different applications. This resistance has little effect in the circuit, but is included for completeness. The stimulus crosstalk drives the measurement amplifiers through the electrode/tissue interface. This interface is shown in FIG. 4 as a set of series capacitance/resistance pairs, modelling a component referred to in the literature as a "Warburg element". The RC pairs model the complex diffusion behaviour at the electrode surface, and have time constants from micro-seconds to seconds. The cables from the electrode to the amplifier add capacitance which loads the electrode, along with the resistive input impedance of the amplifier itself. Typical loading would be 200 pF of capacitance and 1 megohms of resistance. Following this is an ideal amplifier in this equivalent circuit of FIG. 4.

The electrode artefact is the response of the electrode/tissue interface, when driven by the stimulus crosstalk and loaded by the capacitance and resistance at the amplifier input. It can be observed, either with a circuit simulator or in a laboratory. It can also be observed that the sign of the artefact is opposite for capacitive and resistive loading. Electrical artefact usually also arises from the behaviour of the amplifier circuitry in response to these particular circumstances.

It is possible to reduce artefact by reducing the loading on the electrode, however in practical situations there are limits to how low this capacitance can be made. Increasing the electrode surface area also decreases artefact but again in practical situations there will be limits to the electrode size. Artefact can also be reduced by adding resistance or capacitance to the amplifier input relying on the opposite sign of the artefact produced by these terms. However, this only works to a limited extent, and changing the size of the electrode changes the size of the required compensation components which makes it difficult to make a general purpose amplifier that can be connected to a range of electrodes. One can also reduce artefact by reducing the size of the stimulus crosstalk, and this is the aim of the virtual ground circuit embodiment of this invention shown in FIG. 5, which relates to evoking and measuring a neural response.

Referring again to FIGS. 2 and 3, an appropriate electrical stimulus 202 will induce nerves to fire, and thereby produces an evoked neural response 206. In the spinal cord, the neural response 206 can have two major components: a fast response lasting ~2 ms and a slow response lasting ~15 ms. The slow response only appears at stimulation amplitudes which are larger than the minimum stimulus required to elicit a fast response. Many therapeutic stimuli paradigms seek to evoke fast responses only, and to avoid evoking any slow response. Thus, the neural response of interest for neural response measurements concludes within about 2 ms. The amplitude of the evoked response seen by epidural electrodes is typically no more than hundreds of microvolts, but in some clinical situations can be only tens of microvolts.

In practical implementation a measurement amplifier used to measure the evoked response does not have infinite bandwidth, and will normally have infinite impulse response filter poles, and so the stimulus crosstalk 204 will produce an output 208 during the evoked response 206, this output being referred to as electrical artefact.

Electrical artefact can be in the hundreds of millivolts as compared to a SCP of interest in the tens of microvolts. Electrical artefact can however be somewhat reduced by suitable choice of a high-pass filter pole frequency.

The measurement amplifier output 210 will therefore contain the sum of these various contributions 202-208. Separating the evoked response of interest (206) from the artefacts 204 and 208 is a significant technical challenge. For example, to resolve a 10 µV SCP with 1 µV resolution, and have at the input a 5V stimulus, requires an amplifier with a dynamic range of 134 dB. As the response can overlap the stimulus this represents a difficult challenge of amplifier design.

Figure 5A:
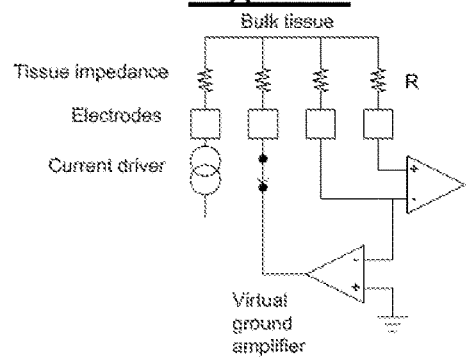
FIG. 5a illustrates a virtual ground system configuration, with double-ended measurement, in accordance with one embodiment of the invention.

FIG. 5a illustrates a neural stimulus and response system providing differential neural measurements and using a shared electrode for measurement and for feedback sense. Alternative embodiments could use two separate electrodes for measurements and feedback sense, respectively.

Figure 5B:
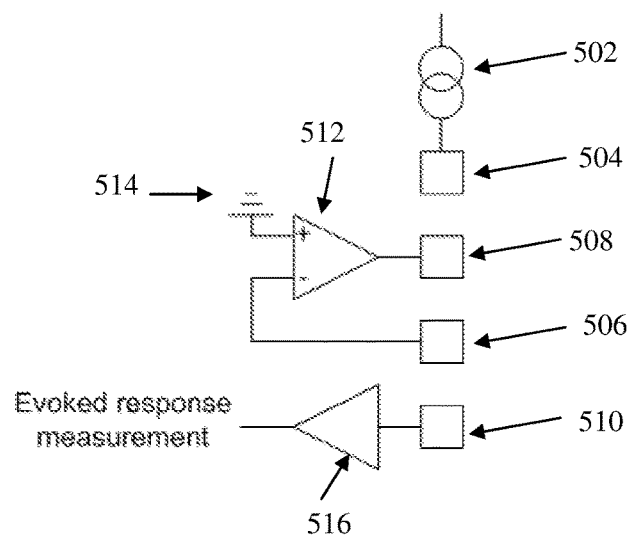
FIG. 5b illustrates a virtual ground system configuration, with single-ended measurement, in accordance with another embodiment of the invention.

FIG. 5b illustrates a configuration of device 100 for controlling electrical conditions of neural tissue in accordance with another embodiment of the present invention, providing single ended neural measurements. In the configuration of FIG. 5b the device has a current source 502 which drives current into tissue via stimulus electrode 504 in order to stimulate the neural tissue and evoke a neural response. A feedback sense electrode 506, compensation electrode 508 and measurement electrode 510 are also provided. The electrodes 504-510 are positioned proximal to neural tissue to make electrical contact with the tissue. A feedback amplifier 512 is referenced to ground 514 and takes as an input a feedback signal from the feedback sense electrode 506. An output of the feedback amplifier 512 is connected to the compensation electrode 508 such that the feedback amplifier 512 is configured to drive the tissue via the compensation electrode 508 in a feedback arrangement which seeks to drive the feedback signal to ground. This mechanism will thus operate to quash stimulus artefact at the tissue electrode interface, improving measurement conditions for neural response measurement circuitry 516.

Figure 5C:
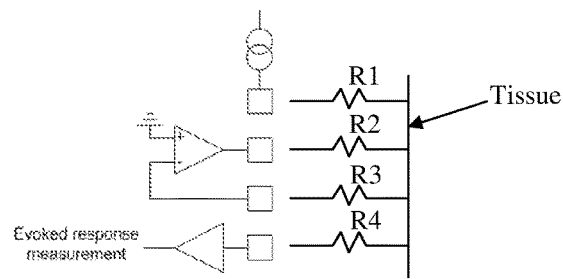
FIG. 5c is a model of the embodiment of FIG. 5b.

As shown in FIG. 5c, the adjacent stimulus, compensation, feedback sense and measurement electrodes in contact with resistive tissue can be modelled as respective contacts each connected to a tissue rail by a respective resistance R1, R2, R3 and R4.

Figure 5D:
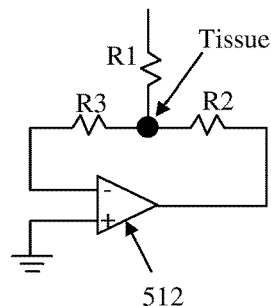
FIG. 5d is an equivalent circuit of the model of FIG. 5c.

An equivalent circuit of FIG. 5c is shown in FIG. 5d. Stimulus and stimulus artefact occurring upon the stimulus electrode creates a current I through R1. Feedback amplifier 512 operates to maintain zero current at each amplifier input, and also operates to maintain the voltage at each input to be identical. Therefore in the configuration of FIGS. 5a-d, the voltage at each amplifier input is zero, because the positive input is referenced to ground. Moreover, current through R3 is forced to zero, being the same as the input current to the amplifier 312. This ensures that there is no voltage differential across R3, and that the tissue node must therefore be forced to ground, in this model. This effect is referred to herein as providing a virtual ground.

The voltage caused by the current stimulus travels at the speed of light in the tissue medium, whereas an evoked action potential in the neural tissue travels at around 60 m/s. When the feedback sense electrode is subject to (or senses) the evoked response it will cancel the stimulus crosstalk in the tissue, but due to the larger propagation delay, the voltages produced by the evoked response at different electrodes (such as the measurement electrodes) will differ, and can be recorded. It will simply be the voltage that would otherwise by recorded as the difference between the measurement electrode and the feedback sense electrode. Alternatively, the sense electrode can be placed elsewhere in the tissue further from the stimulus electrode(s), and substantially no cancellation of the evoked response will then occur, although the electrode will be subject to other electrical signals in the body from muscles, and other nerve bundles. This might be the situation when the sense electrode is on the body of an implant, with the stimulating electrodes on a lead.

Figure 6:
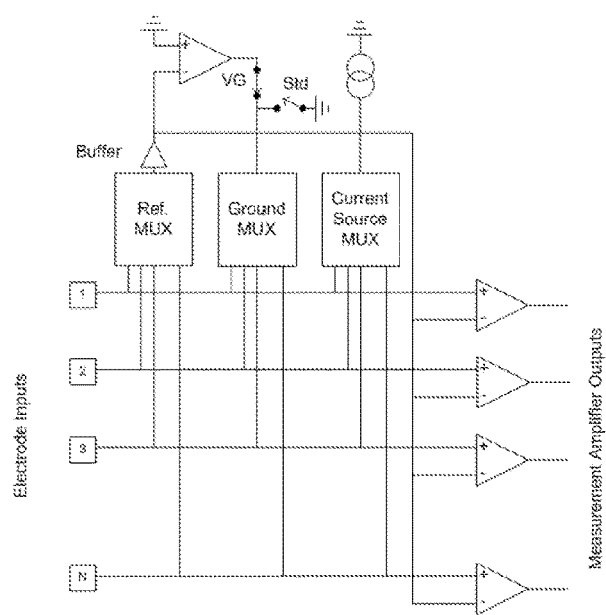
FIG. 6 is a system schematic illustrating multiplexing of virtual ground functionalities across multiple electrodes.

FIG. 6 is a system schematic illustrating multiplexing of virtual ground functionalities across multiple electrodes, applicable to the embodiment of FIG. 5a or FIG. 5b. This shows the buffer at the output of the reference MUX. A set of electrodes is connected to a current source and a set of amplifiers. The "current source MUX" allows the stimulus current to be directed to any electrode. The "Ground MUX" allows any electrode to be chosen as the second of the pair of stimulating electrodes. Switches "Std" and "VG" allow the circuit to selectively provide conventional stimulation, or stimulation according to this invention. A third multiplexor selects the electrode to be used as the reference point (feedback sense electrode). Once the electrode configuration has been chosen, the circuit operates according to FIGS. 5a-d. Each of the N electrodes of the array of FIG. 6 may thus, at any given time, nominally serve as any one of the stimulus, sense or measurement electrode.

The circuit of FIG. 6 may alternatively be modified such that the reference voltage passed to the virtual ground feedback amplifier is a combination of the voltages on the measurement electrodes, e.g. the average of two or more electrode voltages.

In principle, the virtual ground circuit of the embodiment of FIG. 5b provides for the stimulus electrode 504 to be driven by a current source. An op-amp circuit 512 and compensating electrode 508 provides a feedback loop holding the tissue voltage, as measured at a sense electrode 510, to 0 V. In an ideal situation, the voltage on the compensating electrode 508 is identical in amplitude but of opposite polarity to the voltage on the stimulating electrode 504. This ideally leaves the potential on a measurement electrode 510 unchanged by the stimulation and thus significantly improves conditions for measurement of an evoked response with reduced artefact.

Referring to FIG. 6, it is noted that the components making up the virtual ground circuit are spread throughout the device 100, having components in the reference multiplexer (Ref. MUX). As shown in FIG. 6, an electrode is wired to the inverting input multiplexer. This includes a buffer to drive the capacitance on the inputs of the array of amplifiers, and the virtual ground amplifier. These components, their parasitics, and the capacitance of the wiring on the circuit boards from which the system is made must be considered in order to design a stable circuit.

Figure 7A:
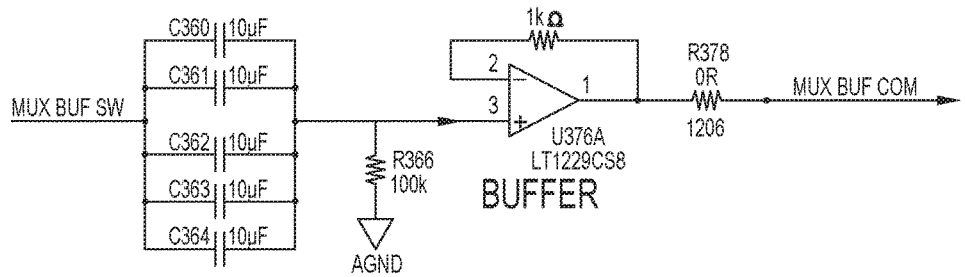
FIG. 7a illustrates an equivalent circuit of the virtual GND embodiment of FIG. 6.

FIG. 7a illustrates the actual circuit used for the amplifier in the reference multiplexer ("Ref. MUX") of FIG. 6, in the preferred embodiment of the virtual ground circuit. The reference signal selected by the MUX is buffered before it is passed to the amplifier negative inputs, and the virtual ground circuit. The buffer uses a current feedback amplifier, because this amplifier is inside the virtual ground feedback loop and this amplifier introduces less phase shift than a voltage feedback device. This has been used both for experimental verification in a saline bath (from which the attached figures were obtained) and in a human subject.

Figure 7B:
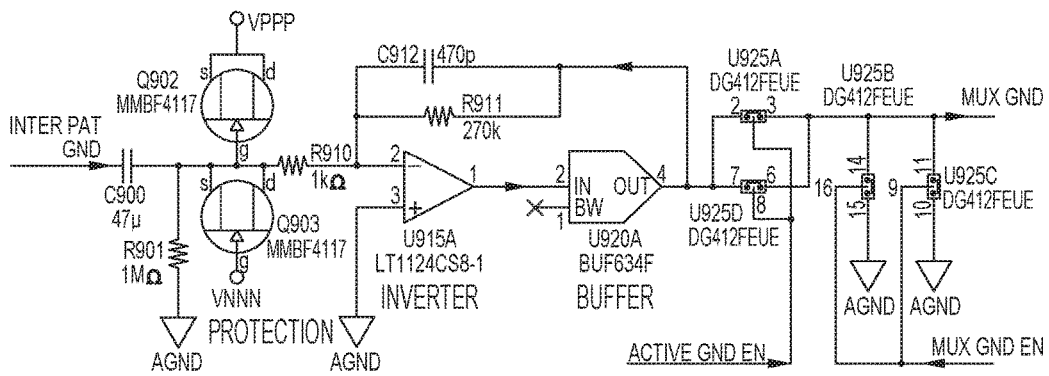
FIG. 7b illustrates an active ground "bridge" driver in accordance with an embodiment of the invention.

As shown in FIG. 7b, the virtual ground circuit of this embodiment includes an inverting amplifier and a high-speed buffer. The op-amp alone does not have the current sourcing capability to drive the current available from the current sources, which can deliver up to 50 mA. The 470 p capacitor provides dominant pole compensation to the loop. The switches are paralleled to provide low impedance paths, and match the switch configuration of FIG. 6.

The FETs Q902 and Q903 in FIG. 7b, from the input to the supplies, provide electrostatic discharge (ESD) protection. The capacitor C900 and pulldown resistor R901 set the DC bias point for the loop.

Figure 8A:
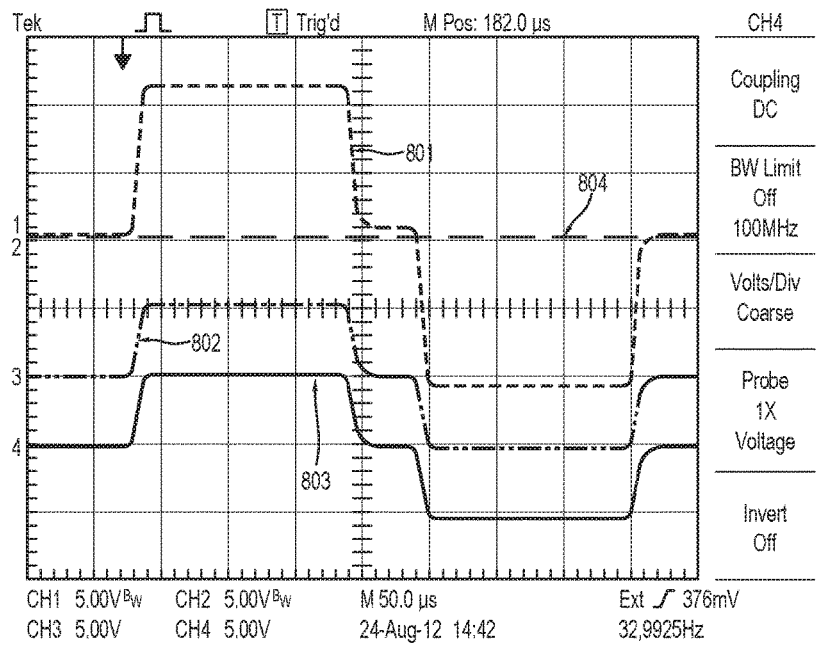
FIG. 8a illustrates the operation of the embodiment of FIG. 6 when the virtual ground function is disabled.

FIG. 8a illustrates the problem of stimulus crosstalk when the virtual ground function is disabled. Trace 801 is from Electrode 1 (stimulus electrode), trace 804 is from Electrode 2 (ground electrode), trace 802 is from Electrode 4 (first measurement electrode), and trace 803 is from Electrode 5 (second measurement electrode).

Figure 8B:
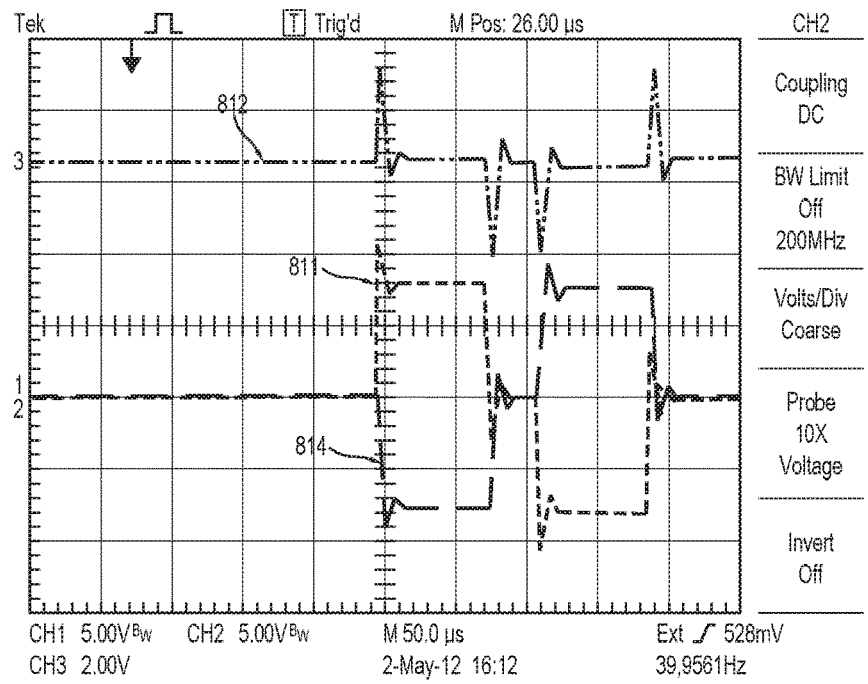
FIGS. 8b and 8c show the operation of the circuit of FIG. 6 when the virtual ground function is activated, when experimentally demonstrated on a bench using a saline bath.
Figure 8C:
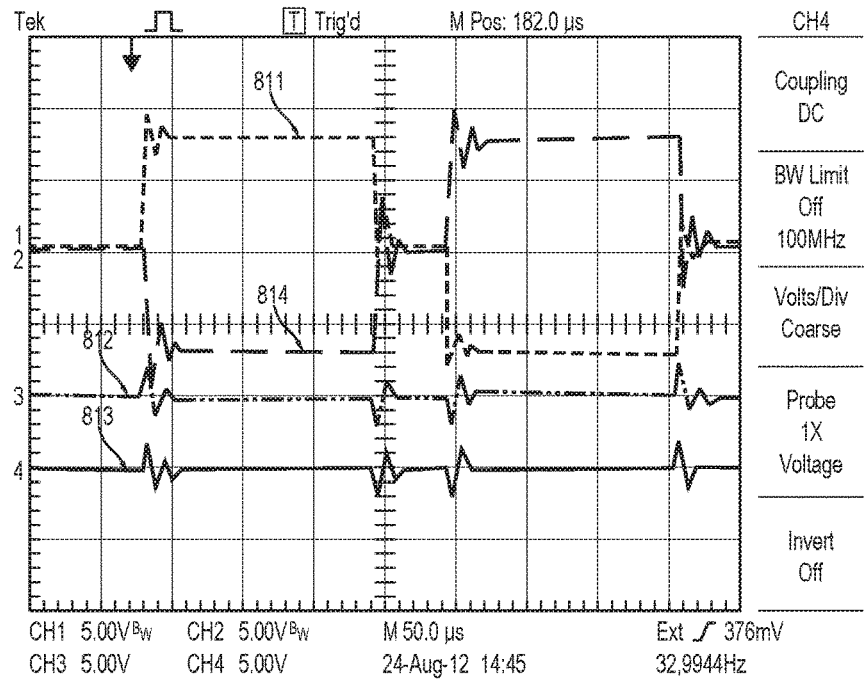

FIGS. 8b and 8c show the behaviour of the circuit of FIG. 6 when the virtual ground function is activated, when experimentally implemented on a bench using an actual saline bath. FIGS. 8b and 8c show the response to a 10 mA biphasic pulse stimulus in $\frac{1}{10}$ PBS (phosphate buffered saline). As can be seen, now the stimulus and feedback electrodes (811 and 814) swing in opposite directions, while the measurement electrodes (812 and 813) mostly stay at ground. The ringing at the measurement electrodes is the response of the feedback loop to the very high slew-rate current source edges, but represents significantly reduced artefact as compared to FIG. 8a.

Figure 9A:
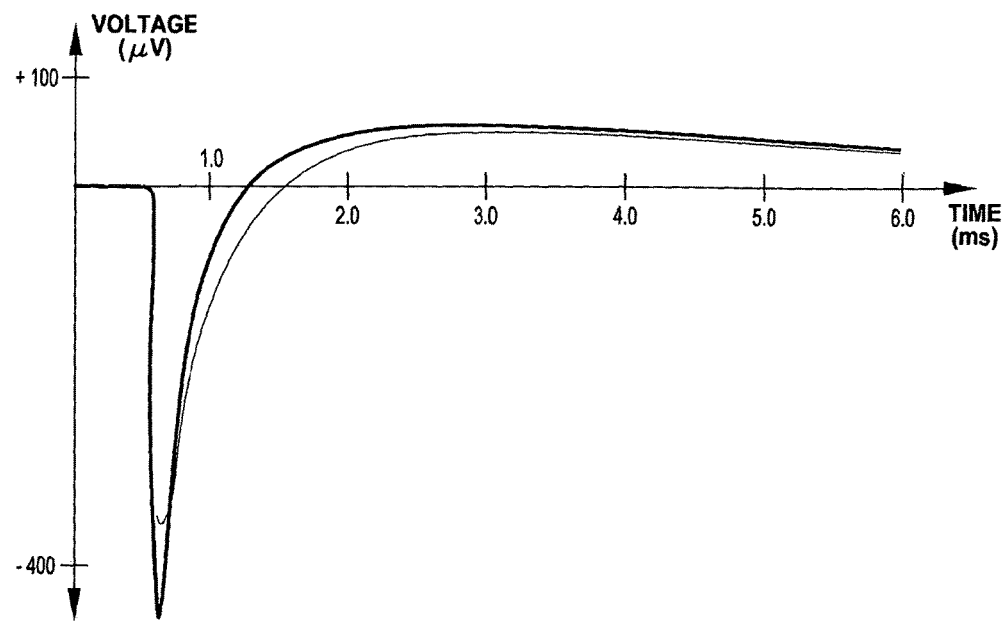
FIG. 9a illustrates the operation of the embodiment of FIG. 6 when the virtual ground function is disabled, with amplifier blanking.

FIG. 9a shows artefact with virtual ground disabled, and in particular shows the behaviour of the circuit of FIG. 6 when the virtual ground function is deactivated, when experimentally implemented on a bench using an actual saline bath. In FIG. 9a, the stimulus occurred and concluded at some time prior to t=0.6 ms, at which time the amplifiers were blanked. The amplifiers were then unblanked at t=0.6 ms. FIG. 9 shows the measured voltages on two measurement electrodes, with a peak artefact of around 400 uV.

Figure 9B:
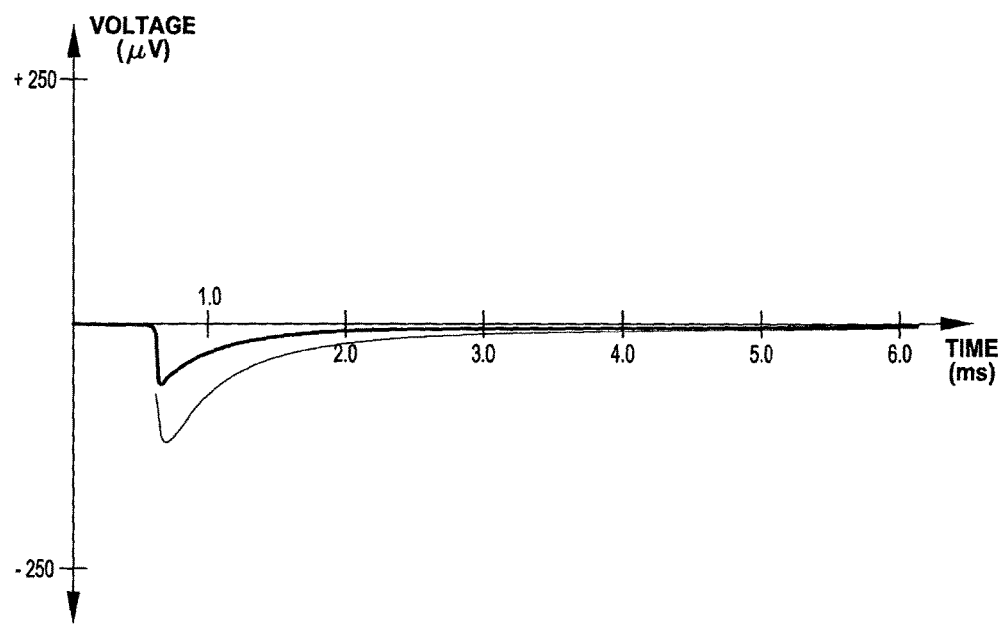
FIG. 9b illustrates the step response of the embodiment of FIG. 6 when the virtual ground function is enabled, with amplifier blanking.

FIG. 9b shows the amplifier outputs with virtual ground enabled, but otherwise identical stimulation as produced FIG. 9a. As can be seen, when using virtual ground in the circuit of FIG. 6, artefact is about 100 uV, or smaller by about 75%.

Figure 10A:
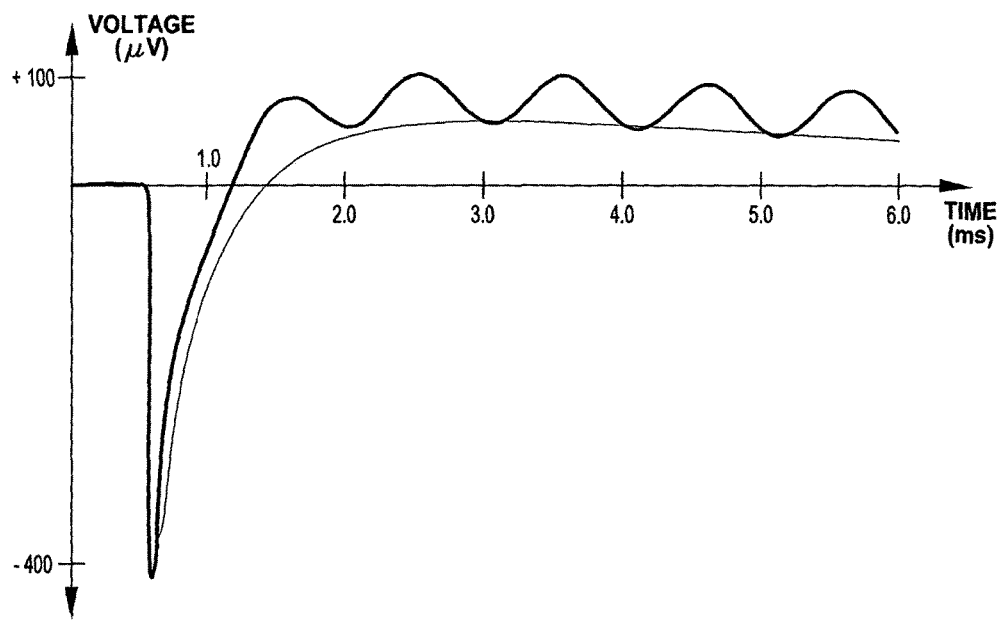
FIG. 10a illustrates the performance of the embodiment of FIG. 6 when the virtual ground function is disabled, with amplifier blanking and sinusoid injection.

FIG. 10a shows the amplifier output for the same experiment as FIG. 9a, but with a 50 uV pp sinusoidal signal injected in series with electrode 4, to give an idea of how an evoked response would superimpose upon the artefact. The sinusoidal signal cannot be easily seen before about 1.5 ms, i.e. the first 1 ms of measurement time is obscured by the artefact.

Figure 10B:
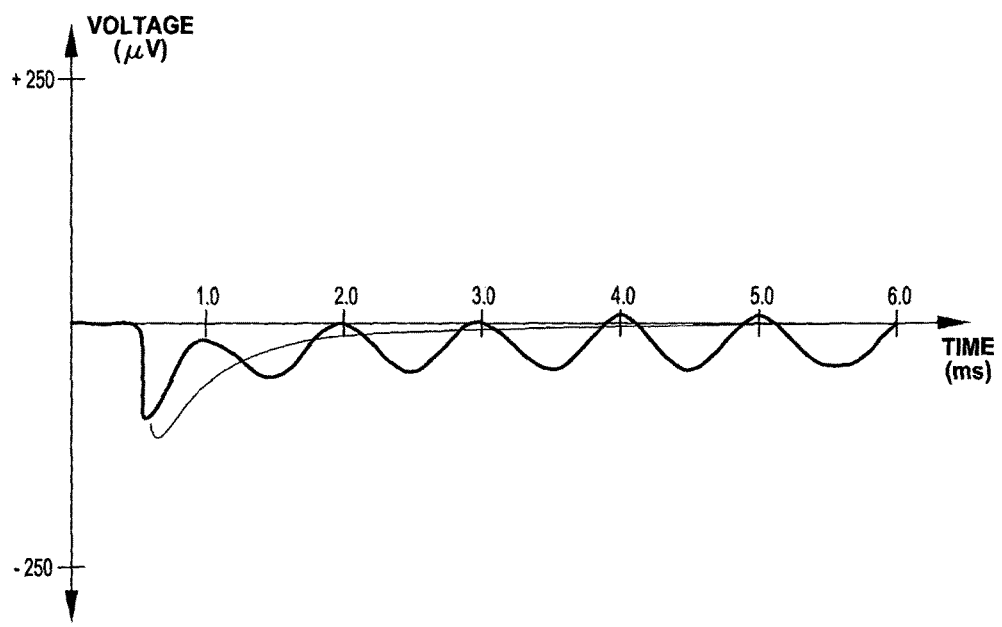
FIG. 10b illustrates the step response of the embodiment of FIG. 6 when the virtual ground function is enabled, with amplifier blanking and sinusoid injection.

FIG. 10b is for the same experiment as FIG. 10a but with virtual ground enabled. Here, the sinusoidal signal can be seen distinct from the artefact from around 0.75 ms, or about 750 us (80%) earlier than for FIG. 10a relative to the unblanking time.

Figure 11A:
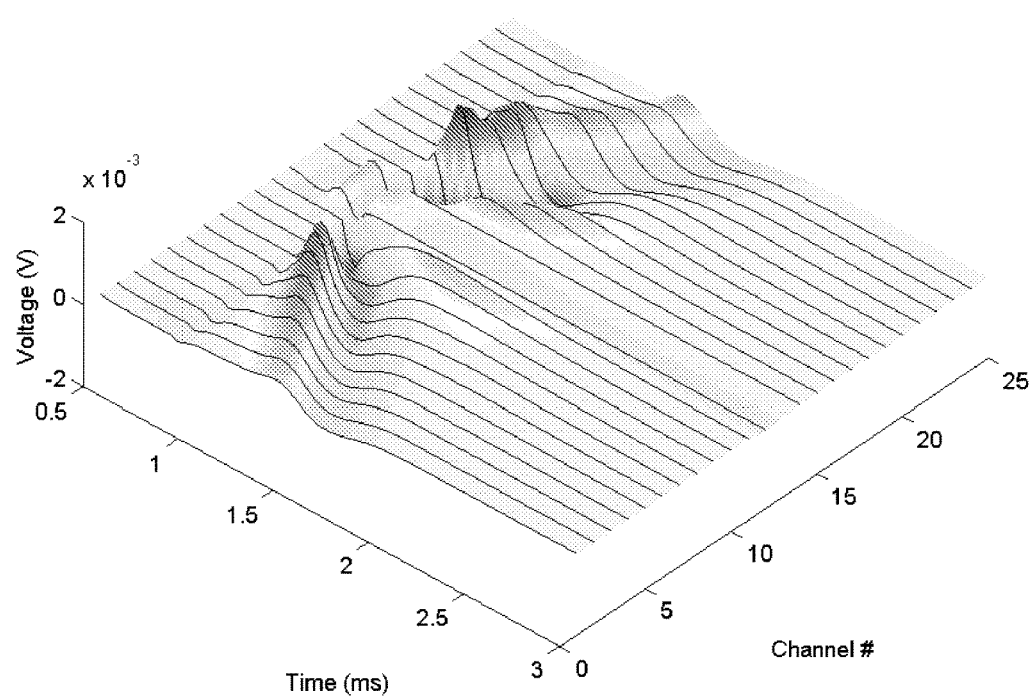
Figure 11B:
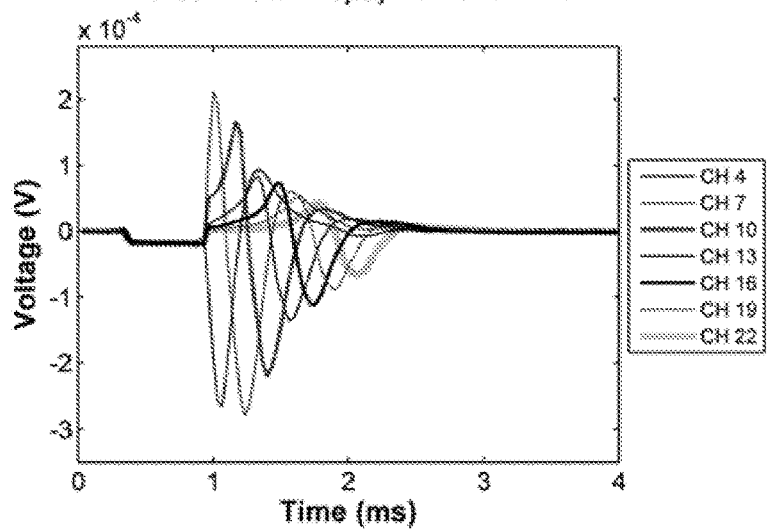
FIG. 11b is a superimposed plot of similar data, demonstrating timing of respective signal features.

FIG. 11a shows the evoked response in a sheep dorsal column. In particular, FIG. 11a plots the measurements obtained simultaneously from 22 electrodes of a 24 electrode array in response to a stimulus delivered by two adjacent electrodes positioned centrally in the array. As can be seen, evoked responses propagate simultaneously both caudally and rostrally from the central stimulus site. The current required to evoke such a response in a sheep is much lower than in humans, and the evoked response signals are higher, so artefact is less of a problem. In other regards the sheep signals are similar to the human case. In FIG. 11a the amplifiers are unblanked at approximately 0.75 msec and the response finishes within another 0.75 ms. FIG. 11b is a superimposed plot of similar data, demonstrating timing of respective signal features when measuring on multiple electrodes at increasing distance from the stimulus site. FIGS. 11a and 11b illustrate the importance of reducing artefact during the period immediately after stimulation.

In a first mode of operation in accordance with some embodiments of the invention, at the end of stimulation the stimulation electrodes are both disconnected. The bath (or subject) is floating at this point, as there is no connection between the bath and the circuit ground. Since the amplifiers are all differential, taking the difference between the reference electrode and the other epidural electrodes will compensate for any change in voltage. This mode of operation reflects the logic that other choices of which electrode to ground seem likely to worsen artefact: connecting a stimulation electrode will cause the bath potential to change as the electrode voltage settles; connecting an epidural electrode to GND might put a transient on it which would be seen on all the channels.

In a second mode of operation of other embodiments of the invention, the VG circuit remains active after the stimulation, which makes the bioelectrical situation quite different. The voltage on the compensation electrode will change as the electrode potentials settle, but the VG loop will compensate for this so it will not affect the bath potential. At the same time, the VG circuit can hold the bath at a fixed voltage—GND. The VG circuit will attempt to keep the epidural space at a static voltage, namely GND.

In another embodiment, the present invention is implemented in an application-specific integrated circuit (ASIC). The primary difference that is encountered in an ASIC implementation is that whereas most PCB amplifiers and components are intended for split supply operation, most ASIC designs, especially one intended for implantable operation, will operate from a single supply. Also, in an ASIC, the desire to produce a low-cost design is increased, as an ASIC implementation would be preferable for commercial exploitation.

Figure 12:
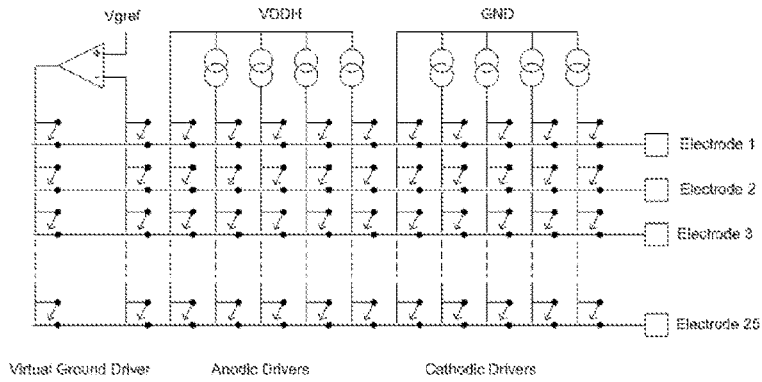
FIG. 12 illustrates an alternative embodiment intended for ASIC implementation.

FIG. 12 shows a design intended for ASIC operation. The design uses separate current sources to provide anodic and cathodic current. These are connected to an electrode array. They also electrodes to be arbitrarily connected to the output and input of the virtual ground amplifier. The point "Vgref" provides the bias point for the amplifier; this would typically be half the power supply. In this case the power supply is called "VDDH", indicating it is a high-voltage supply suitable for tissue stimulation.

The switched connections directly to VDDH and GND allow stimulation modes that do not use the virtual ground amplifier. In the design of FIG. 5a, the virtual ground amplifier provides the entire current for the second of the two stimulating electrodes. To create the ASIC implementation some changes were required. In the PCB design of FIG. 5a, the amplifier output provides the entire opposite current to that of the output of the current driver. This requires an amplifier with a considerable output drive, for example if the current source can drive 50 mA, so must the amplifier. An amplifier with this current drive, stable in a feedback loop, and with the required bandwidth can be difficult to obtain, although they are available.

Figure 13:
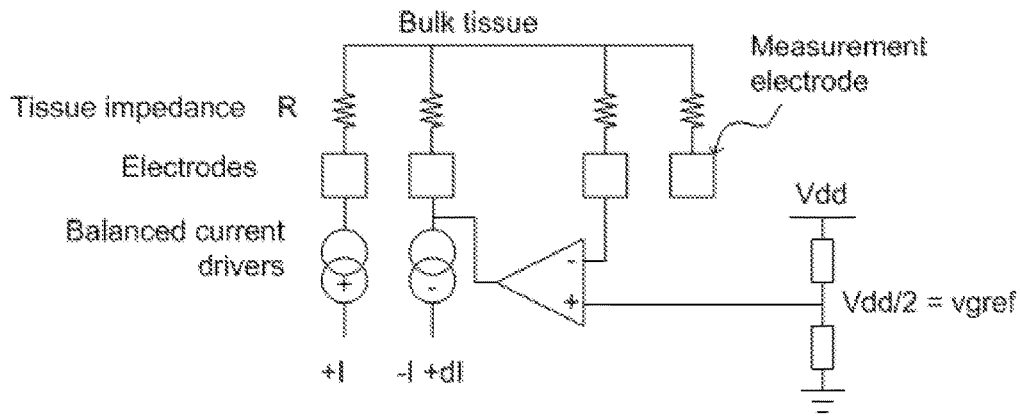
FIG. 13 illustrates another embodiment intended for ASIC implementation.

Thus a problem in an ASIC implementation is to provide the virtual ground amplifier with sufficient current capability to balance the current source; this takes considerable silicon area which incurs cost. Noting that both positive and negative current sources are available in the ASIC, the present embodiment thus uses the circuit of FIG. 13, suitable for integrated circuit implementation. This implementation requires the use of matched positive and negative current drivers. It also operates from a single supply, simplifying the system implementation. The feedback loop holds the tissue voltage at a stable voltage—the midpoint of the two supplies. The amplifier only has to source or sink a current equal to the mismatch between the two amplifiers, denoted dI in FIG. 13. Since the current source has a high output impedance, the load seen by the amplifier is unchanged as compared to the case of FIG. 5a where the amplifier provides all the drive, however the amplifier no longer has to provide high current. In a case where the current sources match to 10%, a 0.1 reduction in capability is achieved.

Figure 14:
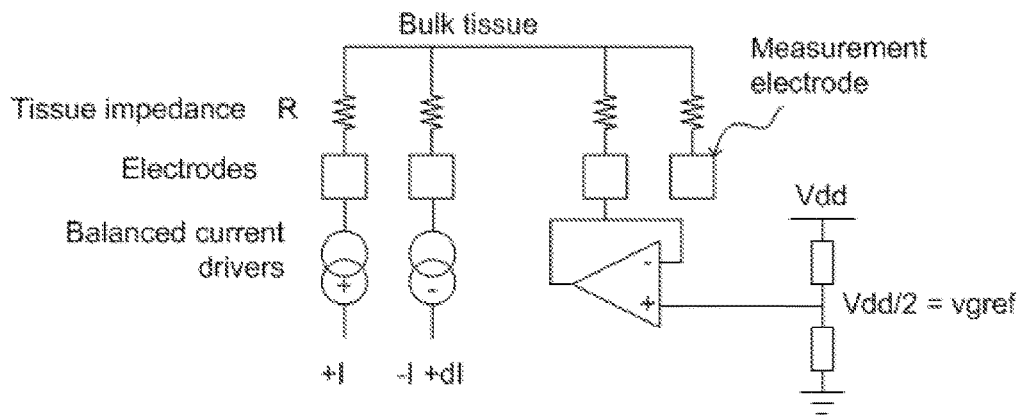
FIG. 14 illustrates yet another embodiment intended for ASIC implementation.

FIG. 14 illustrates yet another embodiment, in which the amplifier is connected as a unity gain buffer. It is noted that this proposal may be integrated into the design of Australian Provisional Patent Application No. 2012904838.

It will be appreciated by persons skilled in the art that numerous variations and/or modifications may be made to the invention as shown in the specific embodiments without departing from the spirit or scope of the invention as broadly described. For example while application of the method to neural stimulation is described, it is to be appreciated that the techniques described in this patent apply in other situations involving measurement of a voltage within tissue during or after stimulation.

The present embodiments are, therefore, to be considered in all respects as illustrative and not restrictive.

The invention claimed is:

1. A method for measuring a neural response to a stimulus, the method comprising:
   providing a plurality of implantable electrodes including at least one nominal stimulus electrode, at least one nominal measurement electrode, at least one nominal feedback sense electrode and at least one nominal compensation electrode, the electrodes being implanted proximal to a neural tissue and being in electrical contact with the neural tissue;
   applying an electrical stimulus to the neural tissue from the at least one stimulus electrode;
   during an application of the stimulus, connecting a feedback signal from the at least one feedback sense electrode to an input of a feedback amplifier, and referencing the feedback amplifier to a desired electrical value;
   during an application of the stimulus, connecting an output of the feedback amplifier to the at least one compensation electrode such that the feedback amplifier drives the neural tissue via the at least one compensation electrode in a feedback arrangement which seeks to drive the neural tissue to the desired electrical value; and
   obtaining a measurement of a neural response from the at least one measurement electrode.

2. The method of claim 1 wherein the desired electrical value is electrical ground referenced to a patient ground electrode distal from the at least one feedback sense electrode.

3. The method of claim 1 wherein, during the entire period of stimulation, the feedback amplifier operates and is in connection with the at least one feedback sense electrode and at least one compensation electrode.

4. The method of claim 1 wherein the at least one feedback sense electrode and the at least one measurement electrode are located outside a dipole formed by the at least one stimulus electrode and the at least one compensating electrode.

5. An implantable device for controlling electrical conditions of tissue, the device comprising:
   a plurality of implantable electrodes including at least one nominal feedback sense electrode, at least one nominal compensation electrode, at least one nominal stimulus electrode, and at least one nominal sense electrode; the electrodes being configured to be implanted proximal to the tissue to make electrical contact with the tissue;
   a stimulus source for providing an electrical stimulus to be delivered from the at least one stimulus electrode to neural tissue;
   measurement circuitry for amplifying a neural signal sensed at the at least one sense electrode; and
   a feedback amplifier configured to be referenced to a desired electrical value and to take as an input a feedback signal from the feedback sense electrode during application of the stimulus, an output of the feedback amplifier being connected to the compensation electrode such that the feedback amplifier is configured to drive the neural tissue via the compensation electrode during application of the stimulus in a feedback arrangement which seeks to drive the feedback signal to the desired electrical value.

6. The device of claim 5 wherein the feedback amplifier is configured to operate in connection with the feedback sense electrode and compensation electrode during an entire period of the electrical stimulus.

7. The device of claim 5 wherein the desired electrical value is electrical ground referenced to a patient ground electrode distal from the feedback sense electrode.

8. The device of claim 5 wherein the feedback sense electrode and the measurement electrode are located outside a dipole formed by the stimulus electrode and the compensating electrode.

* * * * *